| United States Patent [19] | [11] Patent Number: 4,923,874 |
| McMahon et al. | [45] Date of Patent: May 8, 1990 |

[54] USE OF 8-AZAPURIN-6-ONE DERIVATIVES FOR CONTROL OF HYPERTENSION

[75] Inventors: Ellen G. McMahon; Robert E. Manning, both of St. Louis, Mo.

[73] Assignee: G. D. Searle & Co., Chicago, Ill.

[21] Appl. No.: 222,680

[22] Filed: Jul. 21, 1988

[51] Int. Cl.$^5$ ............................................. A61K 31/505
[52] U.S. Cl. ..................................... 514/258; 514/262
[58] Field of Search ................................. 514/262, 258

[56] References Cited

U.S. PATENT DOCUMENTS 3,819,631  6/1974  Broughton et al. .......... 260/256.4 F

OTHER PUBLICATIONS

W. R. Kukovetz et al, *Nauyn–Schmiedeberg's Arch. Pharmacol.*, 310, 129–138 (1979).

W. Martin et al, *J.P.E.T.*, 237(2), 539–547 (1986).
W. Martin et al., *Br. J. Pharm.*, 89, 557–561 (1986).
R. W. Lappe et al., *Circ. Res.*, 56, 606–612 (1985).
R. F. G. Booth et al., *Biochem. Pharm.* 36(20), 3517–3521 (1987).
N. Frossard et al, *Br. J. Pharm.*, 73, 933–938 (1981).
R. M. Rudd, *Br. J. Dis. Chest.*, 77, 78–86 (1983).
J. E. McCormick et al, *Proc. R. Ir. Acad.*, Sect. B, 83, B(1–16), 125–138 (1983).

*Primary Examiner*—Allen J. Robinson
*Attorney, Agent, or Firm*—J. Timothy Keane; Paul D. Matukaitis

[57] ABSTRACT

A class of 8-azapurin-6-one derivatives is described for use in control of hypertension. A compound of particular interest is 8-aza-2-(2-n-propoxyphenyl)purin-6-one.

18 Claims, 17 Drawing Sheets

USE OF 8-AZAPURIN-6-ONE DERIVATIVES FOR CONTROL OF HYPERTENSION

FIELD OF THE INVENTION

This invention is in the field of cardiovascular therapeutics and relates to a class of fused pyrimidine compounds for use in control of hypertension. Of particular interest is a class of 8-azapurin-6-one derivatives for use in lowering blood pressure in hypertensive subjects.

BACKGROUND OF THE INVENTION

It has been known for some time that the vasorelaxant effect of the nitrovasodilators, endothelium-derived relaxing factor (EDRF) and atrial natriuretic peptides is caused by stimulation of guanylate cyclase and an elevation in intracellular cGMP levels in vascular smooth muscle cells. In particular, the effects of 8-azapurin-6-one compounds on vascular smooth muscle have been investigated. For example, the effect of four different nitrovasodilators on cGMP levels and relaxation of bovine coronary artery tissue in the presence of 2-o-propoxyphenyl-8-azapurin-6-one has been investigated [W. R. Kukovetz et al, *Naunyn-Schmiedeberg's Arch. Pharmacol.*, 310, 129–138 (1979)]. In an investigation of the vasorelaxant effects of endothelium derived relaxing factor (ERDF) on rat and rabbit aorta, it was found that 2-o-propoxyphenyl-8-azapurine-6-one potentiated the effects of spontaneously released EDRF [W. Martin et al, *J.P.E.T.*, 237(2), 539–547 (1986)]. The potentiation of atriopeptin-II-induced relaxation of rabbit aorta by 2-o-propoxyphenyl-8-azapurine-6-one has been confirmed [W. Martin et al, *Br. J. Pharm.*, 89, 557–561 (1986)]. In subsequent tests, however, involving an infusion of rat with atriopeptin II, it was found that blood pressure lowering was due to a drop in cardiac output and not due to arterial vasodilation. [R. W. Lappe et al, *Circ. Res.*, 56, 606–612 (1985)]. Thus, in vitro determinations of vasorelaxant activity are not predictive of blood pressure lowering activity in mammals. The inhibitory effects of a class of dibenzoquinazoline diones on cGMP phosphodiesterase from bovine renal artery have been investigated. In this study, it was shown that these compounds lowered blood pressure when injected into spontaneously hypertensive rats. [R. F. G. Booth et al, *Biochem. Pharm.*, 36 (20), 3517–3521 (1987)].

The compound 2-o-propoxyphenyl-8-azapurin-6-one) has been shown to inhibit allergen-stimulated histamine release from mast cells and was initially developed as an orally active prophylactic agent for the treatment of asthma [N. Frossard et al, *Br. J. Pharm.*, 73, 933–938 (1981)]. The mechanism of the mast cell stabilizing effect of this compound is believed to be inhibition of cGMP phosphodiesterase, the enzyme responsible for the metabolism of cGMP, and a subsequent increase in intracellular cGMP levels in mast cells [N. Frossard et al, *Br. J. Pharm.*, 73, 933–938 (1981); R. M. Rudd, *Br. J. Dis. Chest.*, 77, 78–86 (1983)]. U.S. Pat. No. 3,819,631 describes a class of 8-azapurin-6-one compounds, including specifically the compound 2-o-propoxyphenyl-8-azapurin-6-one for use in the treatment of asthma.

Other uses for the compound 2-o-propoxyphenyl-8-azapurin-6-one have been investigated. For example, the antiviral activity of this compound was examined along with other fused pyrimidines [J. E. McCormick et al, *Proc. R. Ir. Acad., Sect. B*, 83, B(1-16), 125–138 (1983)].

DESCRIPTION OF THE INVENTION

Treatment of hypertension in a mammal susceptible to or afflicted with hypertension is accomplished by administering a therapeutically-effective amount of an antihypertensive 8-azapurin-6-one compound selected from a family of compounds of Formula I:

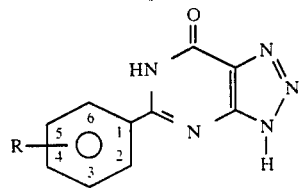

wherein R represents one or more groups selected from alkyl, alkenyl, alkoxy, alkenyloxy, aralkyl and, aralkoxy, the alkyl portion of any of said groups being in linear or branched configuration; or a pharmaceutically-acceptable salt thereof; with the proviso that at least one of R is an alkoxy group.

A preferred class of compounds within Formula I consists of those compounds wherein R represents one or more groups selected from alkyl, alkenyl, alkoxy, alkenyloxy, phenylalkyl and phenylalkoxy, the alkyl portion of any of said groups being in linear or branched configuration and containing one to about twenty carbons, and more preferably one to about ten carbon atoms, or a pharmaceutically-acceptable salt thereof; with the proviso that at least one of R is a linear or branched alkoxy group having one to about twenty carbon atoms, and more preferably one to about ten carbon atoms.

A still more preferred class of compounds within Formula I consists of those compounds wherein R is one or more groups selected from methyl, ethyl, n-propyl, isopropyl, n-butyl, iso-butyl, sec-butyl, tert-butyl, n-pentyl, iso-pentyl, neopentyl, n-hexy, n-heptyl, ethenyl, n-propenyl, iso-propenyl, methoxy, ethoxy, n-propoxy, isopropoxy, n-butoxy, iso-butoxy, sec-butoxy, tert-butoxy, n-pentyloxy, iso-pentyloxy, neopentyloxy, n-hexyloxy, n-heptyloxy, allyloxy, phenmethyl, phenethyl, phenpropyl, phenmethoxy (i.e., benzyloxy), phenethoxy and phenpropoxy; or a pharmaceutically-acceptable salt thereof, with the proviso that at least one of R is an alkoxy group selected from methoxy, ethoxy, n-propoxy, iso-propoxy, n-butoxy, iso-butoxy, sec-butoxy, tert-butoxy, n-pentyloxy, iso-pentyloxy, neopentyloxy, n-hexyloxy, n-heptyloxy, allyloxy and benzyloxy.

A more highly preferred class of compounds of Formula I consists of those compounds wherein R represents one or more groups selected from methyl, ethyl, n-propyl, isopropyl, n-butyl, methoxy, ethoxy, n-propoxy, iso-propoxy, n-butoxy, iso-butoxy, sec-butoxy, tert-butoxy, n-pentyloxy, iso-pentyloxy, neopentyloxy, n-hexyloxy, allyloxy and benzyloxy; or a pharmaceutically-acceptable salt thereof; with the proviso that R includes at least one or two alkoxy groups attached at the 2-,4- or 5- positions of the phenyl ring.

An even more highly preferred class of compounds of Formula I consists of those compounds of Formula 1 listed in Table I.

TABLE I

| Compound # | Formal Name |
|---|---|
| 1 | 8-aza-2-(2-n-propoxyphenyl)purin-6-one |
| 2 | 8-aza-2-(2-methoxyphenyl)purin-6-one |
| 3 | 8-aza-2-(2-ethoxyphenyl)purin-6-one |
| 4 | 8-aza-2-(2-isopropoxyphenyl)purin-6-one |
| 5 | 8-aza-2-(2-n-butoxyphenyl)purin-6-one |
| 6 | 8-aza-2-(2-isobutoxyphenyl)purin-6-one |
| 7 | 8-aza-2-(2-sec-butoxyphenyl)purin-6-one |
| 8 | 8-aza-2-(2-tert-butoxyphenyl)purin-6-one |
| 9 | 8-aza-2-(2-n-pentyloxyphenyl)purin-6-one |
| 10 | 8-aza-2-(2-isopentyloxyphenyl)purin-6-one |
| 11 | 8-aza-2-(2-n-hexyloxyphenyl)purin-6-one |
| 12 | 8-aza-2-(2-benzyloxyphenyl)purin-6-one |
| 13 | 8-aza-2-(2,4-dimethoxyphenyl)purin-6-one |
| 14 | 8-aza-2-(2,5-dimethoxyphenyl)purin-6-one |
| 15 | 8-aza-2-(2,5-dibenzyloxyphenyl)purin-6-one |
| 16 | 8-aza-2-(5-benzyloxy-2-methoxyphenyl)-purin-6-one |
| 17 | 8-aza-2-(5-tert-butyl-2-methoxyphenyl)-purin-6-one |
| 18 | 8-aza-2-(2-methoxy-5-methylphenyl)purin-6-one |
| 19 | 8-aza-2-(2-methoxy-3,5-dimethylphenyl)-purin-6-one |
| 20 | 8-aza-2-(2-allyloxyphenyl)purin-6-one |

The term "alkoxy" is intended to embrace monovalent radicals consisting of an alkyl residue of up to about twenty carbon atoms, whether in linear or ramified (i.e. branched) configuration, which residue is attached to through an oxygen atom to the remainder of the molecule. The term "alkoxy" also embraces radicals having more than one alkyl-oxygen atom, fragments. Thus, the term "alkoxy" as used herein will include those radicals having two or more alkoxy portions, i.e., "alkoxyalkoxy" radicals such as ethoxymethoxy and ethoxyethoxy radicals. The term "alkenyloxy" is analogous to "alkoxy" and embraces alkoxy groups which further include a carbon-carbon double bond so as to make, for example, an allyloxy group. The term "aralkyloxy" is analogous to "alkoxy" and embraces alkoxy groups which further include an aryl radical to make, for example, a benzyloxy group. Where the term "alkyl" is used, alone or within other terms such as "alkenyl" or "aralkyl", the term alkyl embraces linear or branched radicals having one to about twenty carbon atoms, and more preferably one to about ten carbon atoms. "Alkenyl" groups may have one or a plurality of carbon-carbon double bonds, but preferably will contain a single carbon-carbon double bond such as ethenyl and propenyl. "Aryl" groups are exemplified by phenyl and naphthyl, with phenyl preferred.

A most preferred class of compounds of Formula I consists of compounds wherein R is a single alkoxy group selected from methoxy, ethoxy, n-propoxy, n-butoxy and n-pentoxy, attached at the 2- position phenyl ring of Formula I, that is, at the ortho position relative to attachment of the phenyl ring to the 8-azapurine-6-one nucleus, examples of which are included within the compounds listed in Table I namely, compounds #1, #2, #3, #5 and #9.

A most highly preferred compound of Formula I for use in treatment of hypertension is Compound #1 of Table I having the structure below:

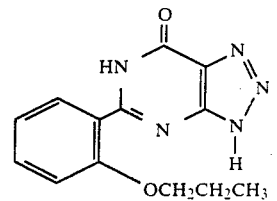

8-aza-2-(2-n-propoxyphenyl)purin-6-one
or
2-ortho-n-propoxyphenyl-8-azapurin-6-one Compounds of Formula I including Compound #1, specifically, may be prepared in accordance with procedures described in U.S. Pat. No. 3,819,631.

Within this class of 8-azapurin-6-one compounds and derivatives of the invention are the pharmaceutically acceptable salts of the compounds of Formula I, including base addition salts. The term "pharmaceutically-acceptable salts" embraces salts commonly used to form alkali metal salts and to form addition salts of free bases. The nature of the salt is not critical, provided that it is pharmaceutically-acceptable. Suitable pharmaceutically-acceptable base addition salts of compounds of Formula I include alkali metal salts, e.g., salts of sodium and potassium, and ammonium salts and amine salts, e.g., salts made from N,N'-dibenzylethylenediamine, chloroprocaine, choline, diethanolamine, trietholanamine, ethylenediamine, diethylamine, triethylamine, meglumine (N-methylglucamine) and procaine. All of these salts may be prepared by conventional means from the corresponding compound of Formula I by reacting, for example, the appropriate base with the compound of Formula I.

Compounds of general Formula I can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. Then, the mixture of diastereoisomers may be resolved by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials. These isomers may be in the form of a free acid, a free base, an ester or a salt. All of these steroisomers, optical isomers, diastereoisomers, as well as mixtures thereof such as racemic mixtures, are within the scope of the invention.

Many therapeutic antihypertensive agents are available for use in reducing blood pressure, such as clonidine, labetalol, metoprolol, minoxidil, prazosin, reserpin and rescinnamine. Also, there are many diuretic agents available which act on the kidney to increase natriuresis and reduce fluid volume, such as amiloride, benzthiazide, bumetanide, chlorothiazide, chlorthalidone, cyclothiazide, ethacrynic acid, furosemide, hydrochlorothiazide, methylclothiazide, metolazone, spironolactone, trichlormethiazide and triamterene. Since all known blood-pressure-lowering agents typically promote sodium retention, because of a drop in pressure at the kidney, a combination of antihypertensive drug and diuretic is required for most patients. In addition a patient suffering from congestive heart failure and edema typically will take a combination of an antihypertensive drug, in order to accomplish blood pressure reduction, and a diuretic agent, in order to reduce fluid volume. An example of one such combination therapy currently available is the blood pressure reducer metoprolol and the diuretic hydrochlorothiazide contained in a single formulation.

An advantage provided by compounds of Formula I in treatment of hypertension is the benefit of simultaneous drop in mean arterial pressure and an increase in natriuresis resulting from the action of a single compound. Compound #1 in particular provides this unexpected combination of properties, that is, a reduction in mean arterial pressure along with an increase in sodium excretion. This combination of properties in one agent eliminates the need for diuretic therapy and may, in particular, provide therapeutic benefit to those hypertensive patients suffering from severe edema.

BRIEF DESCRIPTION OF THE INVENTION

BIOLOGICAL EVALUATION

EXAMPLE I

Figure 1:
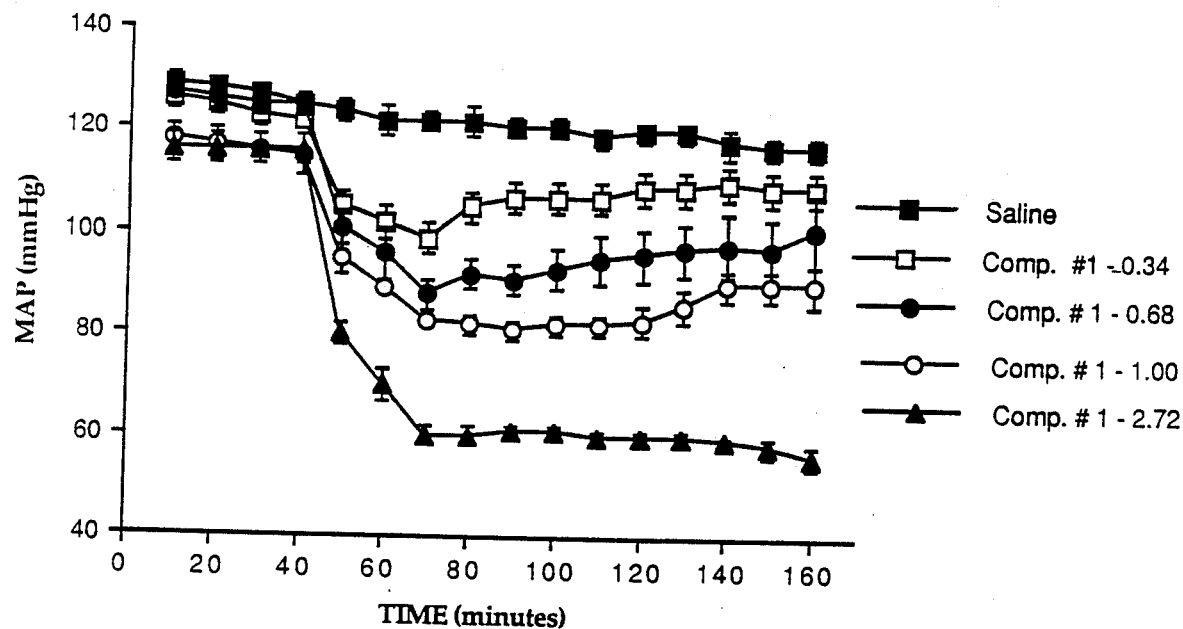
FIG. 1 is a graph showing effects of Compound #1 on mean arterial pressure in anesthetized normotensive rats at four infusion rates.

Compound #1 was infused intravenously into normotensive rats to determine depressor and natriuretic effects by measuring blood pressure and sodium excretion.

Male Sprague Dawley rats (200–350 g) were obtained from Charles River Laboratories and housed in the laboratory animal facility of the McDonnell Sciences Building in laminar flow cage racks. Animals were allowed access to rat chow and water ad libitum until the morning of the experiment. The rats were anesthetized with Inactin (Byk Gulden), 100 mg/kg I.P. A tracheostomy was performed by inserting PE205 polyethylene tubing (1.5–2.0 cm in length) into the trachea about 2–4 mm below the larynx. The right carotid artery and jugular vein were then catheterized using PE 50, and the catheters were filled with heparinized saline (30 U/ml). A PE 205 urine catheter was inserted into the bladder via a midline incision of the abdomen for urine collection throughout the experiment.

Mean arterial pressure was recorded on a Gould system which included Statham transducers (P23ID), universal or pressure processors, pre-amplifiers, and a 2800S 8-channel recorder. The recorder was calibrated each day with a mercury manometer to 50–150 mmHg full scale. Urine was collected in gravimetrically-weighed tubes for 10 minute collection periods. $Na^+$ concentrations were read on an Instrument Laboratories 940 flame photometer and were expressed as uEq/ml. Urine density was assumed to be 1 g/cc.

Thirty-three mg of Compound #1 (M and B 22,948; May and Baker, LTD Batch PSS6) was weighed into a tared 12×75 mm Borosilicate test tube on a Mettler AE240 analytical balance. 0.5 ml of 0.25N NaOH was added and the tube was vortexed vigorously for 2–3 minutes or until the compound dissolved. 5 ul aliquots of 0.05N HCl were then added with continuous vortexing until approximately 50 ul of HCl had been added. The pH of the solution was then measured using a pH indicator strip and was approximately 7.5. The volume of the solution was then measured and an equal volume of distilled water was added to achieve a final concentration of 30 mg/ml.

The rats were allowed to equilibrate for 45–60 minutes following the surgery. An intravenous infusion of 0.9% NaCl was then started at 3 ml/hr to obtain basal urine flow and blood pressure measurements. Forty minutes after the start of the saline infusion the rats received either a continuation of the saline infusion or Compound #1 at 0.34, 0.68, 1.00 or 2.72 mg/kg/min. Solution of Compound #1 were added to the 0.9% NaCl solution and infused at 3 ml/hr for 30 minutes, followed by an infusion of 0.9% NaCl for an additional 90 minutes. Results are reported in Tables II–XI and in FIGS. 1 and 2.

II. EFFECTS OF 0.9% NaCl (3 ML/HR) ON MEAN ARTERIAL PRESSURE IN ANESTHETIZED RATS

| TIME (min) | MAP (mm Hg) | | | | | | | | |
|---|---|---|---|---|---|---|---|---|---|
| | RAT 1 | RAT 2 | RAT 3 | RAT 4 | RAT 5 | RAT 6 | RAT 7 | MEAN | SEM |
| 10 | 122 | 125 | 121 | 130 | 132 | 130 | 140 | 129 | 2 |
| 20 | 121 | 127 | 122 | 127 | 128 | 128 | 140 | 128 | 2 |
| 30 | 120 | 126 | 119 | 127 | 130 | 131 | 139 | 127 | 2 |
| 40 | 120 | 123 | 119 | 123 | 125 | 126 | 139 | 125 | 2 |
| 50 | 116 | 123 | 116 | 122 | 125 | 125 | 138 | 124 | 2 |
| 60 | 116 | 122 | 114 | 118 | 120 | 126 | 137 | 122 | 3 |
| 70 | 117 | 121 | 113 | 120 | 124 | 123 | 135 | 122 | 2 |
| 80 | 118 | 119 | 110 | 123 | 126 | 125 | 136 | 122 | 3 |
| 90 | 118 | 120 | 115 | 114 | 122 | 120 | 135 | 121 | 2 |
| 100 | 120 | 120 | 110 | 122 | 124 | 122 | 132 | 121 | 2 |
| 110 | 115 | 116 | 110 | 120 | 122 | 120 | 128 | 119 | 2 |
| 120 | 120 | 114 | 110 | 122 | 126 | 117 | 132 | 120 | 2 |
| 130 | 118 | 118 | 108 | 120 | 124 | 120 | 130 | 120 | 2 |
| 140 | 117 | 115 | 106 | 115 | 124 | 116 | 132 | 118 | 3 |
| 150 | 118 | 116 | 112 | 110 | 126 | 115 | 124 | 117 | 2 |
| 160 | 113 | 120 | 114 | 108 | 122 | 116 | 125 | 117 | 2 |

III. EFFECTS OF 0.9% NaCl (3 ML/HR) ON URINARY SODIUM EXCRETION IN ANESTHETIZED RATS

| TIME (min) | URINARY SODIUM EXCRETION (uEq/min) | | | | | | | | |
|---|---|---|---|---|---|---|---|---|---|
| | RAT 1 | RAT 2 | RAT 3 | RAT 4 | RAT 5 | RAT 6 | RAT 7 | MEAN | SEM |
| 10 | 0.09 | 0.09 | 0.12 | 0.29 | 0.92 | 0.51 | 0.77 | 0.40 | 0.11 |
| 20 | 0.07 | 0.11 | 0.04 | 0.32 | 0.61 | 0.40 | 0.39 | 0.28 | 0.07 |
| 30 | 0.04 | 0.07 | 0.21 | 0.31 | 0.24 | 0.27 | 0.40 | 0.22 | 0.04 |
| 40 | 0.04 | 0.02 | 0.17 | 0.29 | 0.18 | 0.31 | 0.20 | 0.17 | 0.04 |
| 50 | 0.05 | 0.02 | 0.42 | 0.21 | 0.19 | 0.26 | 0.15 | 0.19 | 0.04 |
| 60 | 0.05 | 0.01 | 0.42 | 0.20 | 0.24 | 0.30 | 0.14 | 0.19 | 0.05 |
| 70 | 0.05 | 0.01 | 0.24 | 0.25 | 0.40 | 0.24 | 0.11 | 0.19 | 0.05 |
| 80 | 0.07 | 0.01 | 0.37 | 0.21 | 0.79 | 0.35 | 0.10 | 0.27 | 0.09 |
| 90 | 0.07 | 0.02 | 0.28 | 0.26 | 1.19 | 0.33 | 0.12 | 0.32 | 0.13 |
| 100 | 0.10 | 0.05 | 0.18 | 0.20 | 0.97 | 0.32 | 0.15 | 0.28 | 0.10 |
| 110 | 0.16 | 0.06 | 0.31 | 0.28 | 2.27 | 0.53 | 0.12 | 0.53 | 0.26 |
| 120 | 0.25 | 0.03 | 0.36 | 0.78 | 4.09 | 1.05 | 0.16 | 0.96 | 0.47 |
| 130 | 0.49 | 0.02 | 2.10 | 0.72 | 3.68 | 0.81 | 0.11 | 1.13 | 0.43 |
| 140 | 0.82 | 0.02 | 1.57 | 2.64 | 3.63 | 1.49 | 0.17 | 1.48 | 0.43 |
| 150 | 1.36 | 0.02 | 1.35 | 1.75 | 4.19 | 3.40 | 0.17 | 1.75 | 0.51 |
| 160 | 1.17 | 0.03 | 1.42 | 2.36 | 5.07 | 6.63 | 0.17 | 2.41 | 0.83 |

IV. EFFECTS OF COMPOUND #1 (0.34 MG/KG/MIN)* ON MEAN ARTERIAL PRESSURE IN ANESTHETIZED RATS

| TIME (min) | MAP (mm Hg) | | | | | |
|---|---|---|---|---|---|---|
| | RAT 1 | RAT 2 | RAT 3 | RAT 4 | MEAN | SEM |
| 10 | 133 | 124 | 120 | 128 | 126 | 2 |
| 20 | 130 | 122 | 117 | 129 | 125 | 2 |
| 30 | 127 | 122 | 116 | 125 | 123 | 2 |
| 40 | 124 | 122 | 115 | 127 | 122 | 2 |
| 50 | 103 | 96 | 112 | 110 | 105 | 3 |
| 60 | 100 | 92 | 110 | 106 | 102 | 3 |
| 70 | 98 | 89 | 106 | 104 | 99 | 3 |
| 80 | 97 | 99 | 112 | 110 | 105 | 3 |
| 90 | 101 | 99 | 112 | 114 | 107 | 3 |
| 100 | 102 | 98 | 113 | 113 | 107 | 3 |
| 110 | 100 | 100 | 115 | 114 | 107 | 3 |
| 120 | 106 | 99 | 114 | 116 | 109 | 3 |
| 130 | 106 | 101 | 113 | 115 | 109 | 3 |
| 140 | 105 | 102 | 114 | 118 | 110 | 3 |
| 150 | 110 | 100 | 113 | 114 | 109 | 3 |
| 160 | 110 | 100 | 115 | 112 | 109 | 3 |

*The Compound #1 infusion was started at 40 minutes and was terminated at 70 minutes.

V. EFFECTS OF COMPOUND #1 (0.34 MG/KG/MIN)* ON URINARY SODIUM EXCRETION IN ANESTHETIZED RATS

| TIME (min) | URINARY SODIUM EXCRETION (uEq/min) | | | | | |
|---|---|---|---|---|---|---|
| | RAT 1 | RAT 2 | RAT 3 | RAT 4 | MEAN | SEM |
| 10 | 0.01 | 0.09 | 0.90 | 0.70 | 0.43 | 0.17 |
| 20 | 0.01 | 0.08 | 0.88 | 0.70 | 0.42 | 0.17 |
| 30 | 0.01 | 0.04 | 1.06 | 0.63 | 0.44 | 0.20 |
| 40 | 0.01 | 0.02 | 0.97 | 0.60 | 0.40 | 0.18 |
| 50 | 0.02 | 0.03 | 1.49 | 1.54 | 0.77 | 0.33 |
| 60 | 0.16 | 0.07 | 1.72 | 2.69 | 1.16 | 0.49 |
| 70 | 0.15 | 0.07 | 1.89 | 2.99 | 1.28 | 0.55 |
| 80 | 0.15 | 0.08 | 4.48 | 2.92 | 1.91 | 0.84 |
| 90 | 0.51 | 0.10 | 7.66 | 3.24 | 2.88 | 1.35 |
| 100 | 1.36 | 0.40 | 9.88 | 4.72 | 4.09 | 1.66 |

-continued

V. EFFECTS OF COMPOUND #1 (0.34 MG/KG/MIN)* ON URINARY SODIUM EXCRETION IN ANESTHETIZED RATS

| TIME (min) | URINARY SODIUM EXCRETION (uEq/min) | | | | | |
|---|---|---|---|---|---|---|
| | RAT 1 | RAT 2 | RAT 3 | RAT 4 | MEAN | SEM |
| 110 | 1.68 | 1.60 | 10.80 | 5.61 | 4.92 | 1.68 |
| 120 | 2.57 | 3.68 | 10.68 | 6.29 | 5.81 | 1.40 |
| 130 | 2.12 | 5.44 | 9.79 | 7.07 | 6.11 | 1.24 |
| 140 | 1.87 | 7.36 | 10.00 | 7.03 | 6.57 | 1.32 |
| 150 | 2.08 | 3.38 | 8.06 | 5.89 | 4.85 | 1.03 |
| 160 | 2.29 | 7.18 | 7.59 | 6.50 | 5.89 | 0.95 |

*The Compound #1 infusion was started at 40 minutes and was terminated at 70 minutes.

VI. EFFECTS OF COMPOUND #1 (0.68 MG/KG/MIN)* ON MEAN ARTERIAL PRESSURE IN ANESTHETIZED RATS

| TIME (min) | MAP (mm Hg) | | | | | |
|---|---|---|---|---|---|---|
| | RAT 1 | RAT 2 | RAT 3 | RAT 4 | MEAN | SEM |
| 10 | 130 | 126 | 126 | 125 | 127 | 1 |
| 20 | 133 | 124 | 122 | 125 | 126 | 2 |
| 30 | 132 | 126 | 118 | 124 | 125 | 2 |
| 40 | 133 | 125 | 120 | 123 | 125 | 2 |
| 50 | 110 | 100 | 96 | 96 | 101 | 3 |
| 60 | 114 | 97 | 88 | 86 | 96 | 5 |
| 70 | 99 | 90 | 84 | 79 | 88 | 3 |
| 80 | 102 | 92 | 87 | 86 | 92 | 3 |
| 90 | 103 | 92 | 86 | 83 | 91 | 3 |
| 100 | 107 | 94 | 88 | 84 | 93 | 4 |
| 110 | 110 | 96 | 90 | 82 | 95 | 5 |
| 120 | 113 | 94 | 92 | 84 | 96 | 5 |
| 130 | 115 | 96 | 91 | 84 | 97 | 5 |
| 140 | 118 | 99 | 92 | 82 | 98 | 6 |
| 150 | 117 | 99 | 91 | 82 | 97 | 6 |
| 160 | 123 | 102 | 96 | 82 | 101 | 7 |

*The Compound #1 infusion was started at 40 minutes and was terminated at 70 minutes.

VII. EFFECTS OF COMPOUND #1 (0.68 MG/KG/MIN)* ON URINARY SODIUM EXCRETION IN ANESTHETIZED RATS

| TIME (min) | URINARY SODIUM EXCRETION (uEq/min) | | | | | |
|---|---|---|---|---|---|---|
| | RAT 1 | RAT 2 | RAT 3 | RAT 4 | MEAN | SEM |
| 10 | 0.30 | 0.15 | 0.73 | 0.15 | 0.33 | 0.11 |
| 20 | 0.27 | 0.10 | 0.58 | 0.16 | 0.28 | 0.08 |
| 30 | 0.54 | 0.08 | 0.56 | 0.12 | 0.33 | 0.10 |
| 40 | 0.53 | 0.07 | 0.90 | 0.20 | 0.43 | 0.14 |
| 50 | 0.60 | 0.10 | 0.71 | 0.64 | 0.51 | 0.11 |
| 60 | 0.85 | 0.28 | 0.72 | 1.58 | 0.86 | 0.21 |
| 70 | 2.40 | 0.73 | 0.89 | 1.20 | 1.31 | 0.29 |
| 80 | 5.43 | 2.92 | 0.58 | 0.91 | 2.46 | 0.87 |
| 90 | 8.30 | 6.97 | 0.98 | 1.38 | 4.41 | 1.46 |
| 100 | 10.53 | 7.96 | 2.32 | 4.23 | 6.26 | 1.43 |
| 110 | 11.95 | 8.74 | 3.94 | 7.39 | 8.01 | 1.28 |
| 120 | 11.56 | 8.20 | 3.43 | 7.52 | 7.68 | 1.29 |
| 130 | 10.71 | 7.41 | 5.82 | 7.13 | 7.77 | 0.81 |
| 140 | 8.65 | 6.65 | 5.78 | 5.88 | 6.74 | 0.52 |
| 150 | 6.86 | 6.46 | 7.72 | 5.33 | 6.59 | 0.38 |
| 160 | 5.76 | 6.17 | 11.34 | 4.24 | 6.88 | 1.20 |

*The Compound #1 infusion was started at 40 minutes and was terminated at 70 minutes.

VIII. EFFECTS OF COMPOUND #1 (1.00 MG/KG/MIN)* ON MEAN ARTERIAL PRESSURE IN ANESTHETIZED RATS

| TIME (min) | MAP (mm Hg) | | | | | |
|---|---|---|---|---|---|---|
| | RAT 1 | RAT 2 | RAT 3 | RAT 4 | MEAN | SEM |
| 10 | 120 | 116 | 126 | 108 | 118 | 3 |
| 20 | 122 | 116 | 124 | 106 | 117 | 3 |
| 30 | 120 | 118 | 123 | 104 | 116 | 3 |
| 40 | 118 | 117 | 123 | 102 | 115 | 4 |
| 50 | 102 | 86 | 102 | 90 | 95 | 3 |
| 60 | 87 | 87 | 92 | 88 | 89 | 1 |
| 70 | 80 | 83 | 87 | 81 | 83 | 1 |
| 80 | 78 | 84 | 84 | 80 | 82 | 2 |
| 90 | 75 | 84 | 87 | 78 | 81 | 2 |
| 100 | 75 | 88 | 87 | 79 | 82 | 2 |
| 110 | 76 | 86 | 85 | 80 | 82 | 2 |
| 120 | 77 | 86 | 88 | 80 | 83 | 3 |
| 130 | 81 | 94 | 90 | 80 | 86 | 3 |
| 140 | 88 | 95 | 95 | 80 | 90 | 3 |
| 150 | 90 | 92 | 96 | 80 | 90 | 3 |
| 160 | 92 | 90 | 101 | 78 | 90 | 4 |

*The Compound #1 infusion was started at 40 minutes and was terminated at 70 minutes.

IX. EFFECTS OF COMPOUND #1 (1.00 MG/KG/MIN)* ON URINARY SODIUM EXCRETION IN ANESTHETIZED RATS

| TIME (min) | URINARY SODIUM EXCRETION (uEq/min) | | | | | |
|---|---|---|---|---|---|---|
| | RAT 1 | RAT 2 | RAT 3 | RAT 4 | MEAN | SEM |
| 10 | 0.06 | 0.21 | 0.23 | 0.17 | 0.17 | 0.03 |
| 20 | 0.10 | 0.16 | 0.25 | 0.16 | 0.17 | 0.02 |
| 30 | 0.05 | 0.18 | 0.25 | 0.16 | 0.16 | 0.03 |
| 40 | 0.03 | 0.15 | 0.32 | 0.15 | 0.16 | 0.05 |
| 50 | 0.27 | 0.10 | 0.26 | 1.74 | 0.59 | 0.30 |
| 60 | 3.36 | 0.04 | 0.68 | 1.35 | 1.36 | 0.56 |
| 70 | 5.22 | 0.04 | 3.27 | 1.00 | 2.38 | 0.90 |
| 80 | 6.03 | 0.11 | 9.02 | 1.23 | 4.10 | 1.61 |
| 90 | 7.29 | 0.92 | 12.76 | 1.58 | 5.64 | 2.15 |
| 100 | 8.31 | 2.86 | 14.79 | 5.33 | 7.82 | 2.00 |
| 110 | 10.46 | 4.41 | 13.29 | 7.70 | 8.97 | 1.47 |
| 120 | 11.34 | 3.86 | 12.16 | 9.20 | 9.14 | 1.45 |
| 130 | 17.59 | 4.03 | 11.77 | 9.77 | 10.79 | 2.17 |
| 140 | 20.06 | 3.50 | 9.53 | 8.87 | 10.49 | 2.68 |
| 150 | 17.09 | 2.53 | 8.47 | 7.35 | 8.86 | 2.35 |
| 160 | 14.27 | 2.50 | 6.92 | 6.79 | 7.62 | 1.89 |

*The Compound #1 infusion was started at 40 minutes and was terminated at 70 minutes.

X. EFFECTS OF COMPOUND #1 (2.72 MG/KG/MIN)* ON MEAN ARTERIAL PRESSURE IN ANESTHETIZED RATS

| TIME (min) | MAP (mm Hg) | | | | | |
|---|---|---|---|---|---|---|
| | RAT 1 | RAT 2 | RAT 3 | RAT 4 | MEAN | SEM |
| 10 | 119 | 108 | 126 | 112 | 116 | 3 |
| 20 | 120 | 107 | 123 | 112 | 116 | 3 |
| 30 | 119 | 110 | 127 | 108 | 116 | 3 |
| 40 | 121 | 108 | 123 | 110 | 116 | 3 |
| 50 | 80 | 82 | 84 | 75 | 80 | 2 |
| 60 | 78 | 66 | 73 | 63 | 70 | 3 |
| 70 | 58 | 57 | 69 | 55 | 60 | 2 |
| 80 | 61 | 55 | 67 | 58 | 60 | 2 |
| 90 | 62 | 58 | 65 | 60 | 61 | 1 |
| 100 | 62 | 58 | 64 | 58 | 61 | 1 |
| 110 | 61 | 58 | 64 | 57 | 60 | 1 |
| 120 | 61 | 58 | 63 | 56 | 60 | 1 |
| 130 | 62 | 60 | 63 | 56 | 60 | 1 |
| 140 | 57 | 60 | 62 | 57 | 59 | 1 |
| 150 | 54 | 59 | 64 | 56 | 58 | 2 |
| 160 | 50 | 58 | 60 | 56 | 56 | 2 |

*The Compound #1 infusion was started at 40 minutes and was terminated at 70 minutes.

| XI. EFFECTS OF COMPOUND #1 (2.72 MG/KG/MIN)* ON URINARY SODIUM EXCRETION IN ANESTHETIZED RATS | | | | | | |
|---|---|---|---|---|---|---|
| TIME | URINARY SODIUM EXCRETION (uEq/min) | | | | | |
| (min) | RAT 1 | RAT 2 | RAT 3 | RAT 4 | MEAN | SEM |
| 10 | 0.10 | 0.17 | 0.15 | 0.07 | 0.12 | 0.02 |
| 20 | 0.06 | 0.14 | 0.19 | 0.08 | 0.12 | 0.02 |
| 30 | 0.08 | 0.12 | 0.12 | 0.11 | 0.11 | 0.01 |
| 40 | 0.06 | 0.11 | 0.13 | 0.14 | 0.11 | 0.01 |
| 50 | 0.10 | 0.18 | 0.06 | 0.14 | 0.12 | 0.02 |
| 60 | — | 0.11 | 0.04 | — | 0.08 | 0.02 |
| 70 | — | — | 0.02 | — | 0.02 | 0.00 |
| 80 | — | — | 0.08 | — | 0.08 | 0.00 |
| 90 | — | — | 0.33 | — | 0.33 | 0.00 |
| 100 | 0.80 | — | 2.22 | — | 1.51 | 0.41 |
| 110 | 2.24 | — | 4.20 | — | 3.22 | 0.57 |
| 120 | 3.20 | — | 5.77 | — | 4.49 | 0.74 |
| 130 | 3.47 | — | 5.77 | — | 4.62 | 0.66 |
| 140 | 2.29 | 0.30 | 5.83 | 0.18 | 2.15 | 1.02 |
| 150 | 0.45 | 0.41 | 4.49 | 0.21 | 1.39 | 0.80 |
| 160 | 0.05 | 0.32 | 2.26 | 0.08 | 0.68 | 0.41 |

*The Compound #1 infusion was started at 40 minutes and was terminated at 70 minutes.

Animals infused with 0.9% NaCl at 3 ml/hr for 160 minutes demonstrated a slight decrease (approximately 10 mmHg) in mean arterial pressure (MAP) (Table II). These animals served as controls for the rats infused with Compound #1. The urinary excretion of Na increased slightly during the 160 minutes of saline infusion in these animals, as shown on Table III. In a second group of rats, Compound #1 was infused during the 40–70 minute period and MAP and urinary sodium excretion (UNaV) were measured and compared to the rats infused with saline. As shown on Table IV, an infusion of Compound #1 at 0.34 mg/kg/min reduced pressure by approximately 20 mmHg, while a 30 minute infusion at 0.68 mg/kg/min resulted in a 30 mmHg fall in mean arterial pressure (Table VI). These infusions of Compound #1 increased the urinary excretion of sodium to peak values of 6.5 and 8.0 uEq/min, respectively (Table V and Table VII). When Compound #1 was infused at 1.00 mg/kg/min, MAP was reduced by approximately 40 mmHg (Table VIII) and a peak value of 11 uEq/min was reached for urinary sodium excretion (Table IX). At the highest infusion rate tested (2.72 mg/kg/min), MAP fell to approximately 60 mm Hg (Table X). At this very low blood pressure, urine flow was so reduced that urine samples could not be obtained from some of the animals for all collection periods. This accounts for the missing values in Table XI. Those animals producing enough urine for sodium measurements demonstrated a peak sodium excretion rate of 4.5 uEq/min (Table XI)—a rate which was still significantly elevated compared to the saline-infused control animals.

Figure 2:
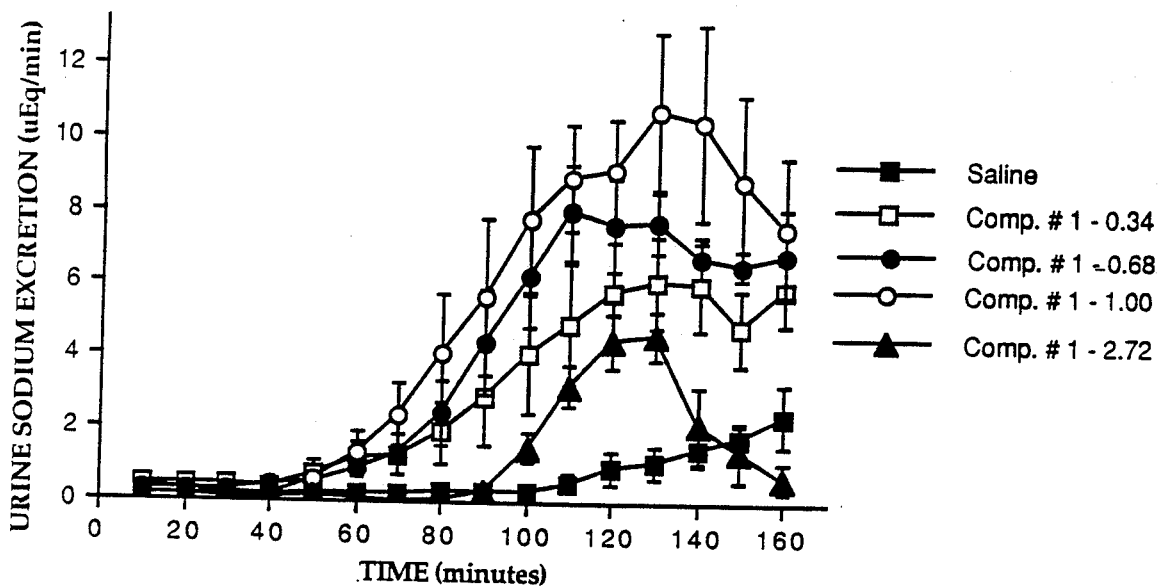
FIG. 2 is a graph showing effects of Compound #1 on urinary sodium excretion in anesthetized normotensive rats at four infusion rates.
Figure 3:
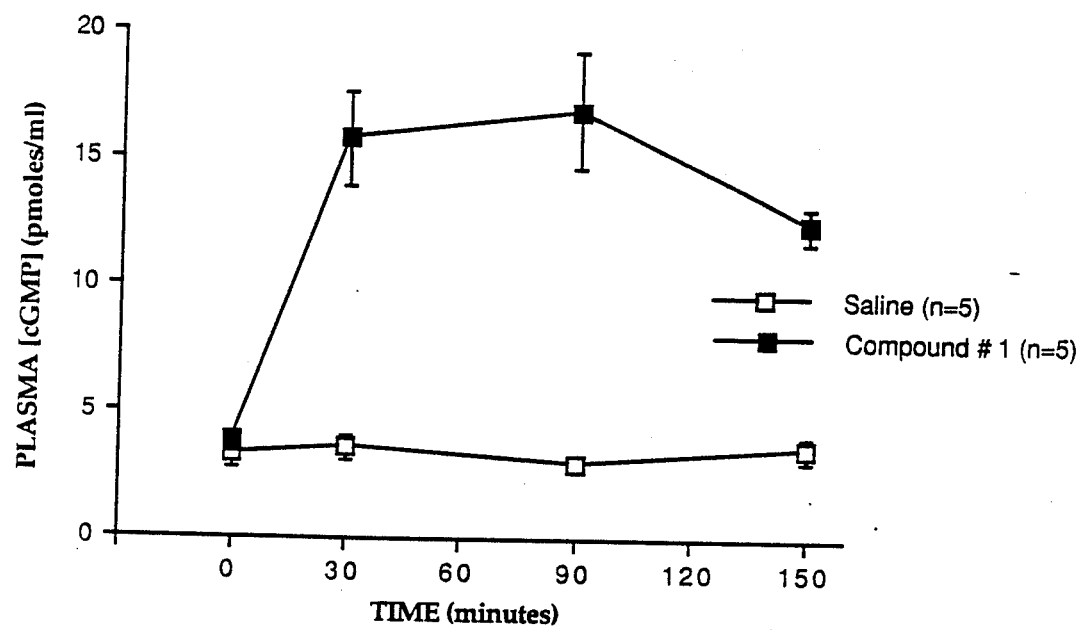
FIG. 3 is a graph showing effect of Compound #1 on levels of plasma cGMP in anesthetized normotensive rats.
Figure 4:
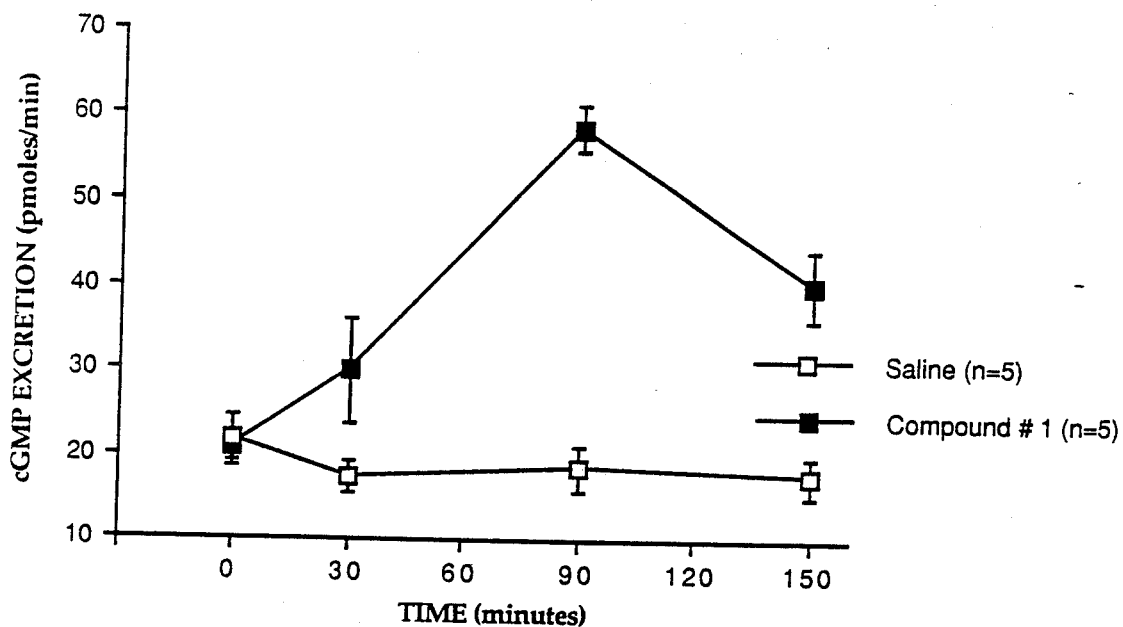
FIG. 4 is a graph showing effect of Compound #1 on urinary excretion of cGMP in anesthetized normotensive rats.
Figure 5:
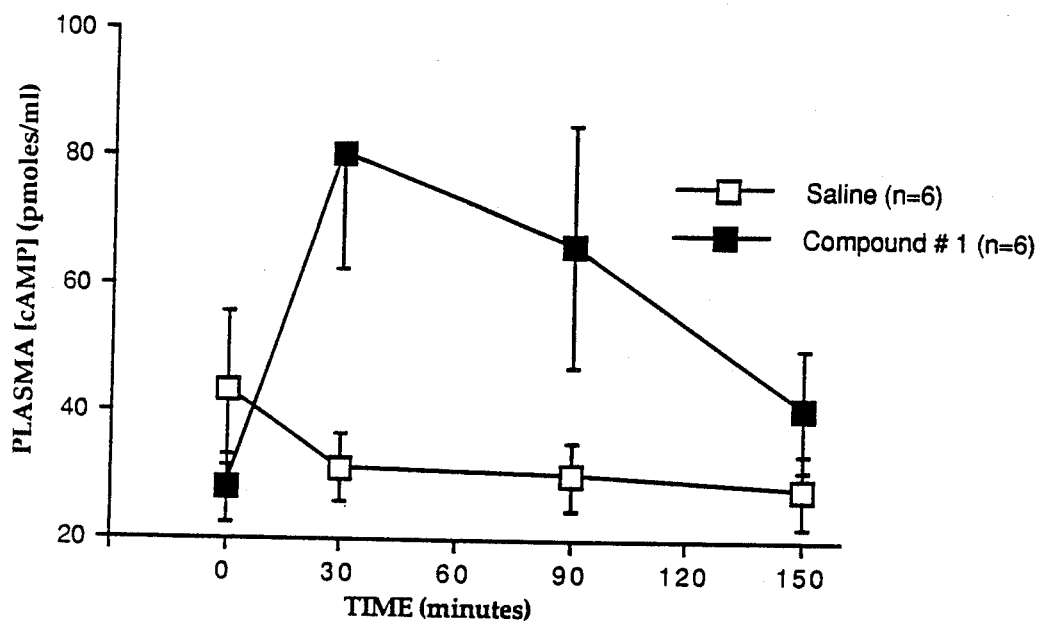
FIG. 5 is a graph showing effect of Compound #1 on levels of plasma cAMP in anesthetized normotensive rats.
Figure 6:
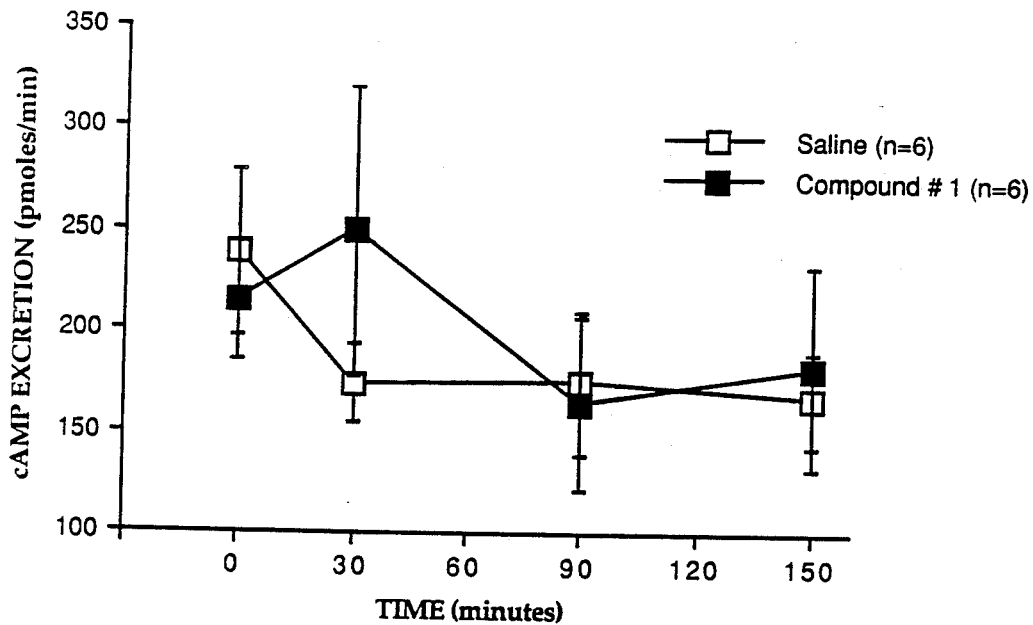
FIG. 6 is a graph showing effect of Compound #1 on urinary excretion of cAMP in anesthetized normotensive rats.

The blood pressure data from these experiments are summarized in FIG. 1 and the sodium excretion data are graphically illustrated in FIG. 2. A thirty minute infusion of Compound #1 into anesthetized rats resulted in a dose-dependent fall in MAP which was reasonably rapid in onset and very prolonged. Although a slight recovery of pressure was observed at the lower infusion rates, at all infusion rates, MAP in the Compound #1-infused rats was significantly lower than pressure in the saline-infused control animals 90 minutes after the Compound #1 infusions were terminated. Urinary sodium excretion was increased significantly at all rates of Compound #1 infusion compared to the saline-infused control rats. However, the increase in UNaV was blunted somewhat in the rats infused at 2.72 mg/kg/min. This was obviously due to the very low blood pressure in these animals (approximately 60 mmHg). While the peak of the depressor response occured at 70 minutes, when the drug infusions were terminated, the natriuretic responses were significantly delayed. Peak natriuretic responses were typically observed between 120 and 140 minutes.

In summary, these data clearly illustrate that Compound #1 infused at 0.34–2.72 mg/kg/min into anesthetized rats results in a significant fall in mean arterial blood pressure. This compound also causes a very prominent simultaneous natriuresis, which reaches its peak value approximately one hour after the fall in pressure reaches its maximum.

EXAMPLE II

In order to determine the mechanism of action of Compound #1, this compound was infused intravenously into normotensive rats to measure cyclic nucleotides (cAMP and cGMP) levels in plasma and urine. Measurements of cAMP and cGMP levels were made in separate groups of test rats.

The test animals were instrumented as described in Example I. A second group of rats (400–500 g) was anesthetized and a PE50 catheter was implanted in the femoral artery of these "donor" rats. 2 ml of blood was drawn from these animals through the femoral artery line and infused into the test rats when blood from the test animals was drawn for measurement of cGMP or cAMP.

Compound #1 was prepared for administration and mean arterial pressure was recorded and urine collected from the test rats as described in Example I. For cGMP plasma samples, an equal volume of ice-cold 10% trichloracetic acid (TCA) was added to the sample and this mixture was centrifuged at 2500 g at about 4° C. for 15 minutes. The supernatant was applied to a 0.6×5.0 cm column of Dowex 50W-X8 (H$^+$), 100–200 mesh, equilibrated with water. The first 4 mls of effluent was collected, lyophilized and then assayed for cGMP using a commercially available radioimmunoassay kit (New England Nuclear). Samples were run in triplicate and extraction efficiencies were consistently greater than 90%. Urine samples were diluted 1/50 and then assayed in triplicate for cGMP. For cAMP, plasma and urine samples were diluted 1/50 and then assayed in triplicate for cAMP using a standard radioimmunoassay kit (New England Nuclear).

The rats were allowed to equilibrate for 45–60 minutes following the surgery. An intravenous infusion of 0.9% NaCl was then started at 3 ml/hr to obtain basal urine flow and blood pressure measurements. Forty minutes after the start of the saline infusion, 2 ml of blood was drawn from the rats for cyclic nucleotide measurements and immediately replaced with 2 ml of blood from the donor rats. The blood was collected in chilled tubes containing 0.1% EDTA and was centrifuged at about 4° C. at 2500 g for 10 minutes. The rats then received either a continuation of the saline or Compound #1 at 1.00 mg/kg/min for 30 minutes. At the end of the 30 minute infusion, a second blood sample was taken. Samples were also taken at 60 and 120 minutes after the Compound #1 infusion was terminated. Urine was collected throughout the experiment every 10 minutes for calculation of urine flow rates and for cyclic nucleotide measurements. Results are reported in Tables XII-XIX and in FIGS. 3-6.

XII. EFFECTS OF 0.9% NaCl (3 ML/HR) ON PLASMA cGMP IN ANESTHETIZED RATS

| TIME (min) | PLASMA cGMP (pmoles/ml) | | | | | | |
|---|---|---|---|---|---|---|---|
| | RAT 1 | RAT 2 | RAT 3 | RAT 4 | RAT 5 | MEAN | SEM |
| 0 | 3.4 | 2.8 | 3.9 | 4.6 | 1.8 | 3.3 | 0.5 |
| 30 | 3.8 | 3.9 | 4.0 | 4.6 | 1.8 | 3.6 | 0.5 |
| 90 | 3.1 | 2.5 | 3.7 | 3.1 | 2.5 | 3.0 | 0.2 |
| 150 | 4.0 | 3.0 | 4.4 | 4.4 | 2.1 | 3.6 | 0.5 |

XIII. EFFECTS OF COMPOUND #1 (1.00 MG/KG/MIN)* ON PLASMA cGMP IN ANESTHETIZED RATS

| TIME (min) | PLASMA cGMP (pmoles/ml) | | | | | | |
|---|---|---|---|---|---|---|---|
| | RAT 1 | RAT 2 | RAT 3 | RAT 4 | RAT 5 | MEAN | SEM |
| 0 | 2.0 | 5.0 | 2.5 | 7.0 | 2.4 | 3.8 | 0.4 |
| 30 | 19.8 | 18.6 | 12.8 | 10.0 | 18.0 | 15.8 | 1.9 |
| 90 | 20.0 | 23.9 | 17.1 | 8.7 | 14.7 | 16.9 | 2.3 |
| 150 | 11.6 | 14.5 | 14.2 | 10.4 | 11.8 | 12.5 | 0.7 |

*The Compound #1 infusion was started at 0 minutes and was terminated at 30 minutes.

XIV. EFFECTS OF 0.9% NaCl (3 ML/HR) ON THE URINARY EXCRETION OF cGMP IN ANESTHETIZED RATS

| TIME (min) | cGMP EXCRETION (pmoles/min) | | | | | | |
|---|---|---|---|---|---|---|---|
| | RAT 1 | RAT 2 | RAT 3 | RAT 4 | RAT 5 | MEAN | SEM |
| 0 | 18.6 | 17.1 | 19.6 | 34.2 | 18.9 | 21.7 | 3.2 |
| 30 | 18.0 | 17.1 | 18.9 | 22.0 | 10.7 | 17.3 | 1.9 |
| 90 | 15.3 | 13.4 | 18.6 | 28.7 | 16.5 | 18.5 | 2.7 |
| 150 | 26.1 | 13.7 | 18.5 | 16.6 | 12.8 | 17.5 | 2.4 |

XV. EFFECTS OF COMPOUND #1 (1.0 MG/KG/MIN)* ON THE URINARY EXCRETION OF cGMP IN ANESTHETIZED RATS

| TIME (min) | cGMP EXCRETION (pmoles/min) | | | | | | |
|---|---|---|---|---|---|---|---|
| | RAT 1 | RAT 2 | RAT 3 | RAT 4 | RAT 5 | MEAN | SEM |
| 0 | 19.5 | 19.9 | 18.5 | 27.4 | 19.6 | 21.0 | 1.6 |
| 30 | 18.0 | 12.3 | 37.8 | 40.4 | 41.5 | 30.0 | 6.2 |
| 90 | 54.1 | 53.4 | 68.3 | 44.1 | 59.2 | 58.7 | 2.7 |
| 150 | 23.4 | 43.5 | 44.1 | 43.4 | 47.1 | 40.3 | 4.3 |

*The Compound #1 infusion was started at 0 minutes and was terminated at 30 minutes.

XVI. EFFECTS OF 0.9% NaCl (3 ML/HR) ON PLASMA cAMP IN ANESTHETIZED RATS

| TIME (min) | PLASMA cAMP (pmoles/ml) | | | | | | | |
|---|---|---|---|---|---|---|---|---|
| | RAT 1 | RAT 2 | RAT 3 | RAT 4 | RAT 5 | RAT 6 | MEAN | SEM |
| 0 | 29.7 | 99.7 | 17.4 | 41.2 | 24.9 | 48.0 | 43.5 | 12.1 |
| 30 | 20.1 | 45.3 | 19.1 | 47.8 | 21.9 | 32.7 | 31.2 | 5.3 |
| 90 | 28.4 | 52.1 | 17.6 | 35.9 | 19.1 | 26.9 | 30.0 | 5.2 |
| 150 | 31.4 | 55.2 | 17.4 | 26.5 | 14.8 | 22.0 | 27.9 | 5.9 |

XVII. EFFECTS OF COMPOUND #1 (1.00 MG/KG/MIN*) ON PLASMA cAMP IN ANESTHETIZED RATS

| TIME (min) | PLASMA cAMP (pmoles/ml) | | | | | | | |
|---|---|---|---|---|---|---|---|---|
| | RAT 1 | RAT 2 | RAT 3 | RAT 4 | RAT 5 | RAT 6 | MEAN | SEM |
| 0 | 40.1 | 35.1 | 34.1 | 3.5 | 22.0 | 32.2 | 27.9 | 5.5 |
| 30 | 101.6 | 135.1 | 118.2 | 50.1 | 39.1 | 37.7 | 80.3 | 17.6 |
| 90 | 96.3 | 106.4 | 120.3 | 30.6 | 20.9 | 22.6 | 66.2 | 18.0 |
| 150 | 55.5 | 78.1 | 44.0 | 25.5 | 16.9 | 23.9 | 40.7 | 9.5 |

*The Compound #1 infusion was started at 0 minutes and was terminated at 30 minutes.

XVIII. EFFECTS OF 0.9% NaCl (3 ML/HR) ON THE URINARY EXCRETION OF cAMP

| TIME (min) | cAMP EXCRETION (pmoles/min) | | | | | | | |
|---|---|---|---|---|---|---|---|---|
| | RAT 1 | RAT 2 | RAT 3 | RAT 4 | RAT 5 | RAT 6 | MEAN | SEM |
| 0 | 309.9 | 173.3 | 151.2 | 217.3 | 405.8 | 175.2 | 238.8 | 40.6 |
| 30 | 173.5 | 219.1 | 122.8 | 140.9 | 144.0 | 244.2 | 174.1 | 19.6 |
| 90 | 103.3 | 238.6 | 81.2 | 112.1 | 223.7 | 288.8 | 174.6 | 35.2 |
| 150 | 139.8 | 263.5 | 110.8 | 121.0 | 194.6 | 169.3 | 166.5 | 23.2 |

XIX. EFFECTS OF COMPOUND #1 (1.00 MG/KG/MIN)* ON THE URINARY EXCRETION OF cAMP

| TIME (min) | cAMP EXCRETION (pmoles/min) | | | | | | | |
|---|---|---|---|---|---|---|---|---|
| | RAT 1 | RAT 2 | RAT 3 | RAT 4 | RAT 5 | RAT 6 | MEAN | SEM |
| 0 | 314.5 | 164.7 | 197.4 | 291.9 | 183.3 | 136.0 | 214.6 | 29.4 |
| 30 | 537.7 | 131.7 | 116.7 | 351.2 | 88.0 | 268.8 | 249.1 | 71.0 |
| 90 | 375.1 | 141.6 | 124.9 | 129.3 | 118.0 | 97.7 | 164.4 | 42.5 |
| 150 | 324.5 | 346.3 | 148.7 | 114.9 | 69.4 | 88.0 | 182.0 | 49.8 |

*The Compound #1 infusion was started at 0 minutes and was terminated at 30 minutes.

This experiment was conducted to determine if an increase in intracellular cGMP concentrations might be involved in mediating the depressor and natriuretic effects of Compound #1 when this compound is infused intravenously into anesthetized rats, as described in Experiment 1. Plasma levels of cGMP remained at a constant level of approximately 3-3.5 pmoles/ml in the rats receiving the saline infusion (Table XII, FIG. 3). In rats receiving Compound #1 at 1 mg/kg/min, plasma levels of cGMP increased significantly from a basal level of around 4 pmoles/ml to 17 pmoles/ml (Table XIII, FIG. 3). This increase in plasma cGMP in the Compound #1 infused animals persisted long after the drug infusion was terminated, just as the blood pressure fall in these rats in response to Compound #1 was persistent (See FIG. 1). The urinary excretion of cGMP was also significantly increased in the rats infused with Compound #1, whereas the excretion of cGMP in the rats receiving saline remained at a stable level of approximately 18-20 pmoles/min throughout the experiment (Table XIV, XV). However, the peak of this increased excretion of cGMP in response to Compound #1 was delayed by approximately one hour compared to the peak increase in plasma cGMP (Table XV, FIG. 4). This is similar to the delay we observed in the natriuretic response to Compound #1 (FIG. 2). In these experiments, the plasma levels of cGMP paralleled the blood pressure lowering response to Compound #1, whereas the urinary excretion of cGMP correlated with the natriuretic action of this drug.

It has been demonstrated that in isolated rat aorta, intracellular levels of cAMP as well as cGMP are increased in response to Compound #1 treatment, although the increase in cGMP is twice as large as the increase in cAMP [(P. Schoeffter et al, Biochem. Pharm., 36:3965-3972, (1987)].

Therefore it was of interest in these experiments to determine whether Compound #1 infused at 1 mg/kg/min also increased plasma levels of cAMP and the urinary excretion of cAMP. Plasma levels of cAMP were increased significantly in the rats infused with Compound #1, compared to the saline-infused control rats (Table XVI, Table XVII and FIG. 5). However, unlike the increase in cGMP plasma levels in response to Compound #1 infusion, the increase in plasma cAMP was transient and did not persist after the drug infusion was terminated. The urinary excretion of cAMP was also transiently elevated in the Compound #1 infused rats (Table XVIII, Table XIX and FIG. 6). Therefore Compound #1 is not 100% selective for cGMP phosphodiesterase, but also probably inhibits cAMP phosphodiesterase in the rat. However, the changes in mean arterial blood pressure and urinary sodium excretion observed with Compound #1 infusion in these studies more closely correlated with the changes in cGMP rather than cAMP. This is suggestive evidence that the physiological effects observed with Compound #1 may be mediated by increases in intracellular cGMP levels.

EXAMPLE III

Compound #1 was infused intravenously into normotensive rats to determine if the blood pressure fall was due to reductions in regional vascular resistance. Male Sprague-Dawley rats (300-425 g), obtained from Harlan Laboratories, were anesthetized with Inactin (Byk Gulden), 100 mg/kg I.P. A tracheostomy was performed by inserting PE205, 1.5-2.0 cm in length into the trachea about 2-4 mm below the larynx. The right femoral artery and the right femoral vein were catheterized using PE50, and the catheters were filled with heparinized saline (30 U/ml). Mean arterial pressure and heart rate were recorded on a Gould system which included Statham transducers (P23ID), universal and pressure processors, pre-amplifiers and a 2800S 8-channel recorder. The recorder was calibrated each day with a mercury manometer such that 0-200 mmHg read full scale.

For regional blood flow measurements, minaturized pulsed-Doppler flow probes (Valpey-Fisher) connected to a Doppler flowmeter (University of Iowa Bioengineering) were used. For placement of the probes, the abdominal cavity was exposed through a midline laparotomy. Four-millimeter lengths of the superior mesenteric, right renal artery and the lower abdominal aorta were then isolated carefully to avoid damage to any nearby nerves. The probe on the lower abdominal aorta monitors blood flow to the hindquarters, which is predominately a measure of skeletal muscle blood flow. Appropriately-sized probes were placed around the isolated blood vessels and loosely secured with 6-0 opthalmic silk. The insulated wire leads of the flow probes were anchored to the abdominal wall, thereby maintaining proper orientation of the probe relative to the vessel. Following closure of the abdominal incision, the wire leads from each probe were connected to the Doppler flow meter.

The Doppler flowmeter system was used to determine blood velocity in kHz Doppler shift, which has been shown to be directly proportional to absolute blood flow as determined with an electromagnetic system [J. R. Haywood et al., Amer. J. Physiol., 241(10): H-273-H-278, (1981)]. An empirical value of relative resistance can be calculated using the following formula:

$$R \text{ or relative resistance (mmHg/kHz)} = \frac{\text{mean arterial pressure (mmHg)}}{\text{Doppler shift (kHz)}}$$

The calculated empirical value is proportional to the absolute resistance in each vascular bed. In addition, changes in vascular resistance can be calculated as the percent change from control by the formula listed below:

$$\% \Delta \text{ in resistance} = \frac{R \text{ during response} - R \text{ baseline}}{R \text{ baseline}} \times 100\%$$

Expressing resistance changes as percent of control allows the opportunity to make meaningful comparisons between animals, despite differences in baseline resistance. Furthermore, by normalizing the data, resistance changes in different vascular beds can be compared.

Compound #1 was prepared for administration as described in Example I. Following instrumentation of the rats, control measurements of each parameter were obtained following sixty minutes of 0.9% NaCl infusion through the femoral vein at 33 ul/min. Compound #1 was then administered in serial doses at 0.34, 1, 2 and 3 mg/kg/min. Each dose was infused iv for fifteen minutes; however, cardiovascular variables were averaged only during the last five minutes of this period. Results are reported in Tables XX–XXVIII and in FIGS. 7–14.

| DOSE (mg/kg/min) | XX. CHANGES IN MEAN ARTERIAL PRESSURE IN RESPONSE TO COMPOUND #1 INFUSION IN ANESTHETIZED RATS Δ MAP (mm Hg) | | | | | | | | | | | |
|---|---|---|---|---|---|---|---|---|---|---|---|---|
| | RAT 1 | RAT 2 | RAT 3 | RAT 4 | RAT 5 | RAT 6 | RAT 7 | RAT 8 | RAT 9 | RAT 10 | MEAN | SEM |
| 0.34 | −1 | −7 | −5 | −14 | −3 | −6 | 0 | −1 | −30 | −14 | −8 | 3 |
| 1.00 | −8 | −18 | −18 | −24 | −15 | −15 | −9 | −11 | −41 | −26 | −19 | 3 |
| 2.00 | −24 | −33 | −42 | −43 | −30 | −41 | −33 | −30 | −56 | −48 | −38 | 3 |
| 3.00 | −34 | −48 | −62 | −51 | −49 | −52 | −45 | −47 | −67 | −67 | −52 | 3 |

XXI. CHANGES IN HEART RATE IN RESPONSE TO COMPOUND #1 INFUSION IN ANESTHETIZED RATS

| DOSE (mg/kg/min) | HEART RATE (beats/min) | | | | | | | | | | MEAN | SEM |
|---|---|---|---|---|---|---|---|---|---|---|---|---|
| | RAT 1 | RAT 2 | RAT 3 | RAT 4 | RAT 5 | RAT 6 | RAT 7 | RAT 8 | RAT 9 | RAT 10 | | |
| 0.34 | 14 | −8 | 34 | −5 | −1 | 17 | 11 | 3 | −22 | −6 | 4 | 5 |
| 1.00 | 26 | −8 | 58 | 7 | −13 | 18 | 30 | 14 | −10 | −4 | 12 | 7 |
| 2.00 | 28 | −8 | 50 | 18 | 4 | 9 | 43 | 18 | −11 | −2 | 15 | 7 |
| 3.00 | 30 | 2 | 47 | 43 | 21 | 20 | 46 | 28 | −3 | 4 | 24 | 6 |

XXII. EFFECTS OF COMPOUND #1 ON MEAN ARTERIAL PRESSURE IN ANESTHETIZED RATS

| DOSE (mg/kg/min) | MAP (mm Hg) | | | | | | | | | | MEAN | SEM |
|---|---|---|---|---|---|---|---|---|---|---|---|---|
| | RAT 1 | RAT 2 | RAT 3 | RAT 4 | RAT 5 | RAT 6 | RAT 7 | RAT 8 | RAT 9 | RAT 10 | | |
| Control | 92 | 110 | 127 | 121 | 114 | 116 | 111 | 113 | 124 | 130 | 116 | 3 |
| 0.34 | 111 | 110 | 107 | 122 | 116 | 94 | 91 | 103 | 114 | 112 | 108 | 3 |
| 1.00 | 99 | 98 | 97 | 109 | 104 | 83 | 84 | 92 | 102 | 102 | 97 | 3 |
| 2.00 | 84 | 75 | 78 | 85 | 82 | 68 | 68 | 77 | 102 | 83 | 80 | 3 |
| 3.00 | 65 | 64 | 70 | 65 | 63 | 57 | 58 | 62 | 66 | 65 | 64 | 1 |

XXIII. EFFECTS OF COMPOUND #1 ON MESENTERIC BLOOD FLOW IN ANESTHETIZED RATS

| DOSE (mg/kg/min) | MESENTERIC BLOOD FLOW (kHz) | | | | | | MEAN | SEM |
|---|---|---|---|---|---|---|---|---|
| | RAT 1 | RAT 2 | RAT 3 | RAT 4 | RAT 5 | RAT 6 | | |
| Control | 5.0 | 4.6 | 0.82 | 1.5 | 4.4 | 4.7 | 3.5 | 0.8 |
| 0.34 | 5.9 | 5.3 | 0.91 | 1.8 | 5.2 | 6.4 | 4.3 | 0.9 |
| 1.00 | 6.0 | 6.3 | 0.95 | 1.8 | 5.9 | 6.4 | 4.6 | 1.0 |
| 2.00 | 6.1 | 6.6 | 0.82 | 1.65 | 6.2 | 5.9 | 4.5 | 1.1 |
| 3.00 | 5.4 | 6.0 | 0.61 | 1.55 | 5.2 | 6.2 | 4.2 | 1.0 |

XXV. EFFECTS OF COMPOUND #1 ON RENAL BLOOD FLOW IN ANESTHETIZED RATS

| DOSE (mg/kg/min) | RENAL BLOOD FLOW (kHz) | | | | MEAN | SEM |
|---|---|---|---|---|---|---|
| | RAT1 | RAT2 | RAT3 | RAT4 | | |
| Control | 4.0 | 3.2 | 3.9 | 2.7 | 3.5 | 0.3 |
| 0.34 | 4.2 | 3.7 | 4.0 | 2.9 | 3.7 | 0.3 |
| 1.00 | 4.2 | 3.85 | 3.9 | 2.75 | 3.7 | 0.3 |
| 2.00 | 2.9 | 3.25 | 3.4 | 2.05 | 2.9 | 0.3 |
| 3.00 | 2.0 | 2.5 | 2.6 | 1.85 | 2.2 | 0.2 |

XXVI. EFFECTS OF COMPOUND #1 ON MESENTRIC RESISTANCE IN ANESTHETIZED RATS

| DOSE (mg/kg/min) | % Δ MESENTERIC RESISTANCE | | | | | | MEAN | SEM |
|---|---|---|---|---|---|---|---|---|
| | RAT1 | RAT2 | RAT3 | RAT4 | RAT5 | RAT6 | | |
| 0.34 | −15 | −18 | −13 | −27 | −19 | −31 | −21 | −3 |
| 1.00 | −24 | −39 | −26 | −34 | −36 | −36 | −33 | −2 |
| 2.00 | −40 | −51 | −32 | −42 | −49 | −48 | −44 | −3 |
| 3.00 | −41 | −57 | −30 | −45 | −52 | −57 | −47 | −4 |

XXIV. EFFECTS OF COMPOUND #1 ON HINDQUARTERS BLOOD FLOW IN ANESTHETIZED RATS

| DOSE (mg/kg/min) | HINDQUARTERS BLOOD FLOW (kHz) | | | | | | MEAN | SEM |
|---|---|---|---|---|---|---|---|---|
| | RAT1 | RAT2 | RAT3 | RAT4 | RAT5 | RAT6 | | |
| Control | 4.5 | 2.3 | 2.4 | 3.8 | 2.2 | 2.1 | 2.9 | 0.4 |
| 0.34 | 5.7 | 2.6 | 2.6 | 5.0 | 2.25 | 2.45 | 3.4 | 0.6 |
| 1.00 | 5.8 | 2.6 | 2.45 | 4.7 | 2.1 | 2.25 | 3.3 | 0.6 |
| 2.00 | 4.9 | 2.5 | 1.9 | 4.0 | 2.15 | 2.0 | 2.9 | 0.56 |
| 3.00 | 4.7 | 2.9 | 1.78 | 3.1 | 2.27 | 1.8 | 2.8 | 0.4 |

XXVII. EFFECTS OF COMPOUND #1 ON HINDQUARTERS RESISTANCE IN ANESTHETIZED RATS

| DOSE (mg/kg/min) | HINDQUARTERS RESISTANCE | | | | | | MEAN | SEM |
|---|---|---|---|---|---|---|---|---|
| | RAT1 | RAT2 | RAT3 | RAT4 | RAT5 | RAT6 | | |
| 0.34 | −22 | −16 | −10 | −33 | −4 | −20 | −18 | 4 |
| 1.00 | −28 | −25 | −14 | −35 | −8 | −19 | −22 | 4 |
| 2.00 | −33 | −35 | −12 | −38 | −23 | −31 | −29 | 4 |
| 3.00 | −39 | −54 | −29 | −28 | −44 | −36 | −38 | 4 |

| XXVIII. EFFECTS F COMPOUND #1 ON RENAL RESISTANCE IN ANESTHETIZED RATS | | | | | | |
|---|---|---|---|---|---|---|
| DOSE | % Δ RENAL RESISTANCE | | | | | |
| (mg/kg/min) | RAT1 | RAT2 | RAT3 | RAT4 | MEAN | SEM |
| 0.34 | −4 | −13 | −26 | −17 | −15 | 5 |
| 1.00 | −14 | −24 | −33 | −21 | −23 | 4 |
| 2.00 | −4 | −28 | −36 | −18 | −22 | 7 |
| 3.00 | 20 | −25 | −32 | −30 | −17 | 12 |

Figure 7:
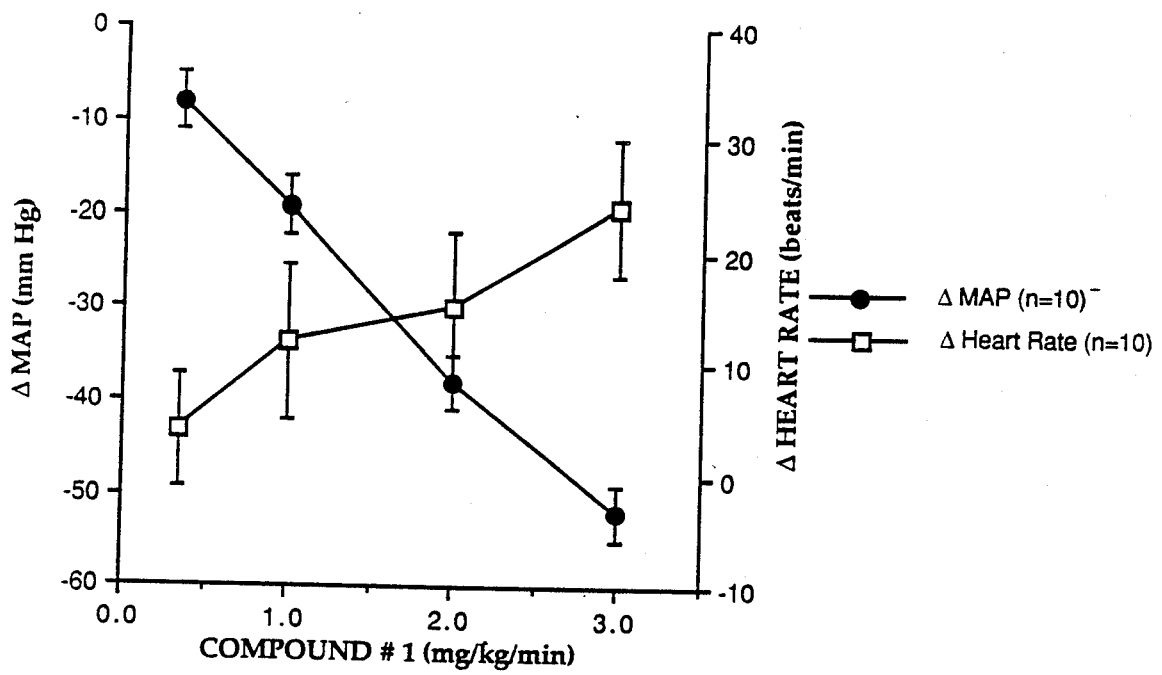
FIG. 7 is a graph showing changes in blood pressure and heart rate in anesthetized normotensive rats infused with Compound #1.
Figure 8:
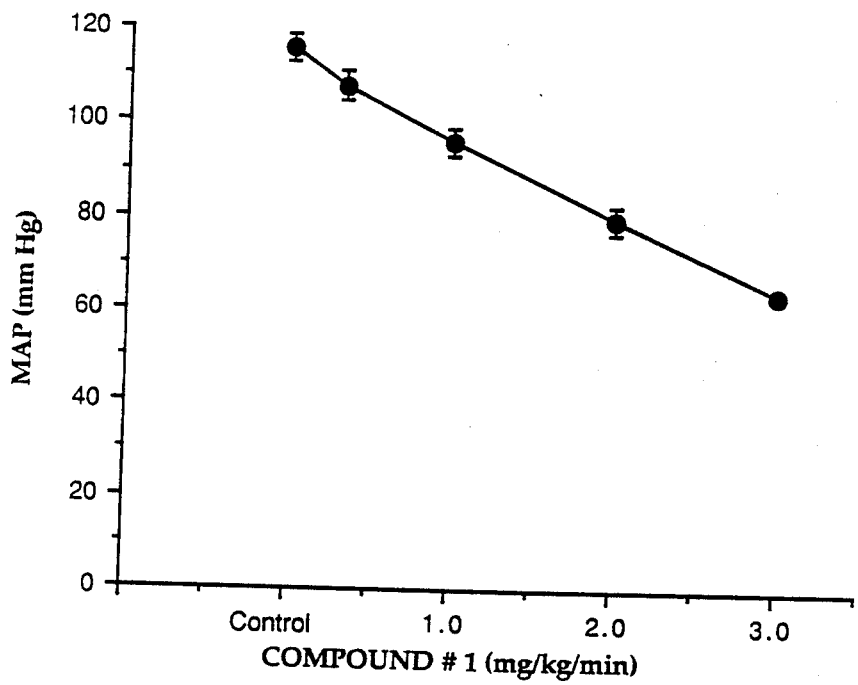
FIG. 8 is a graph showing effects of Compound #1 on blood pressure in anesthetized normotensive rats.
Figure 9:
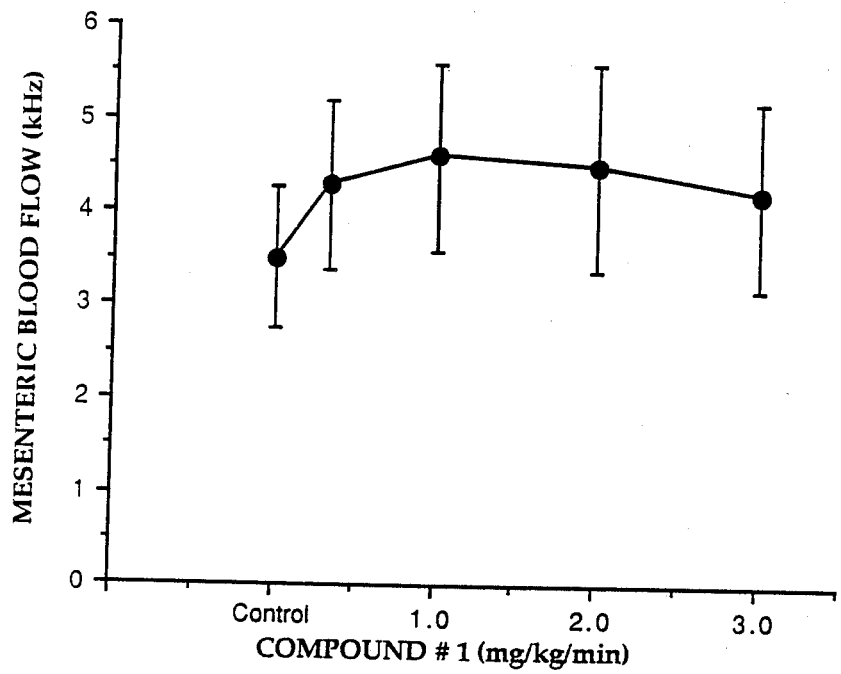
FIG. 9 is a graph showing effects of Compound #1 on mesenteric blood flow in anesthetized normotensive rats.
Figure 10:
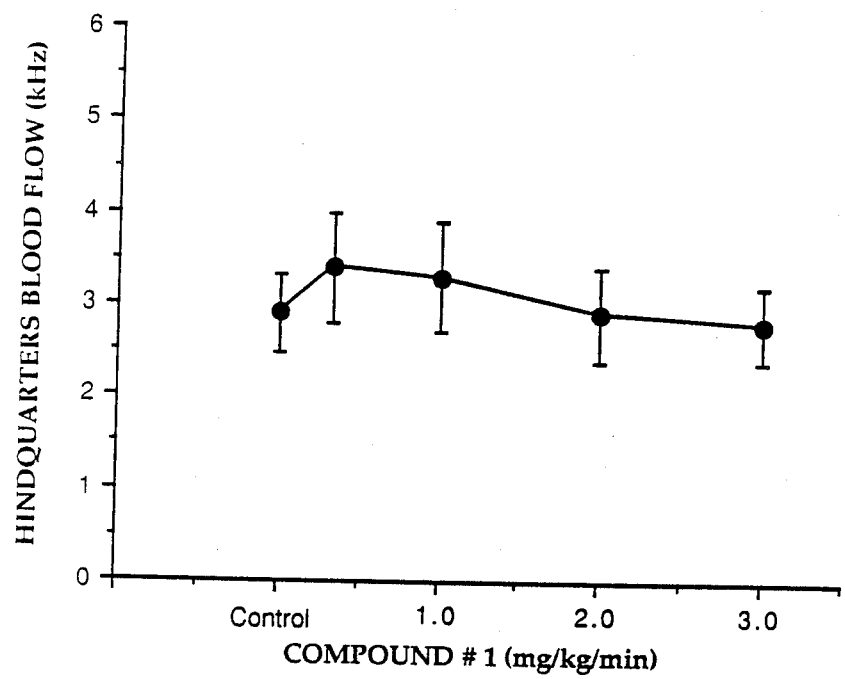
FIG. 10 is a graph showing effects of Compound #1 on hindquarters blood flow in anesthetized normotensive rats.
Figure 11:
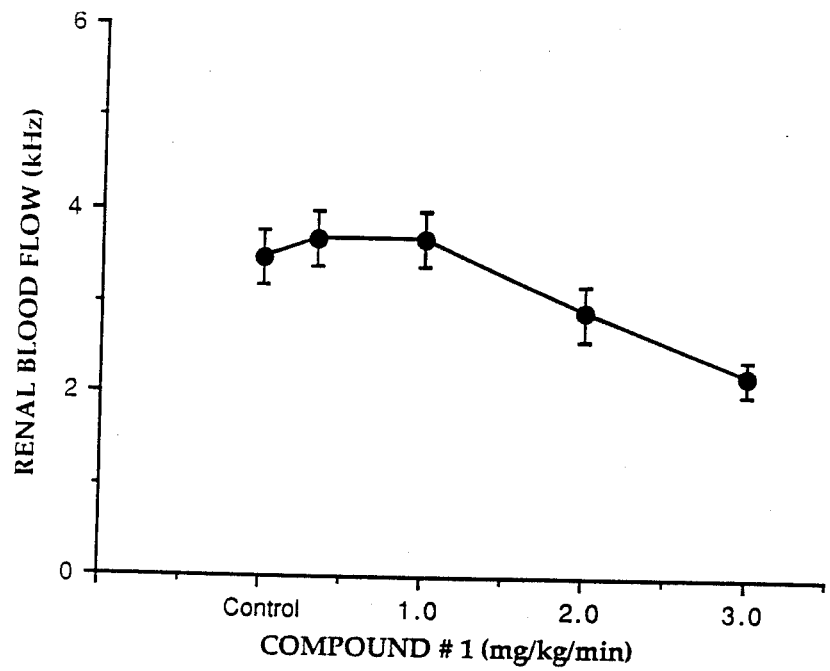
FIG. 11 is a graph showing effects of Compound #1 on renal blood flow in anesthetized normotensive rats.
Figure 12:
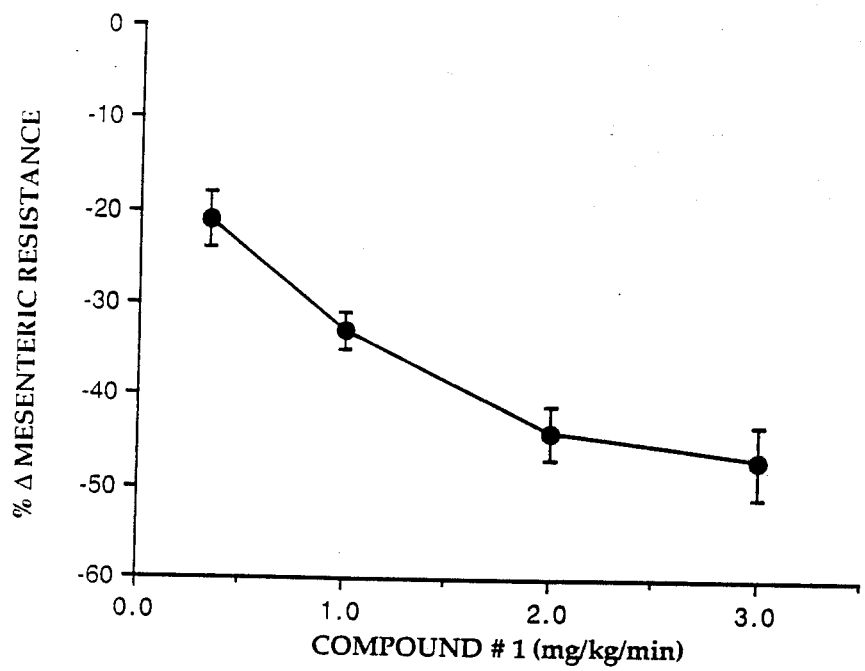
FIG. 12 is a graph showing effects of Compound #1 on mesenteric vascular resistance in anesthetized normotensive rats.
Figure 13:
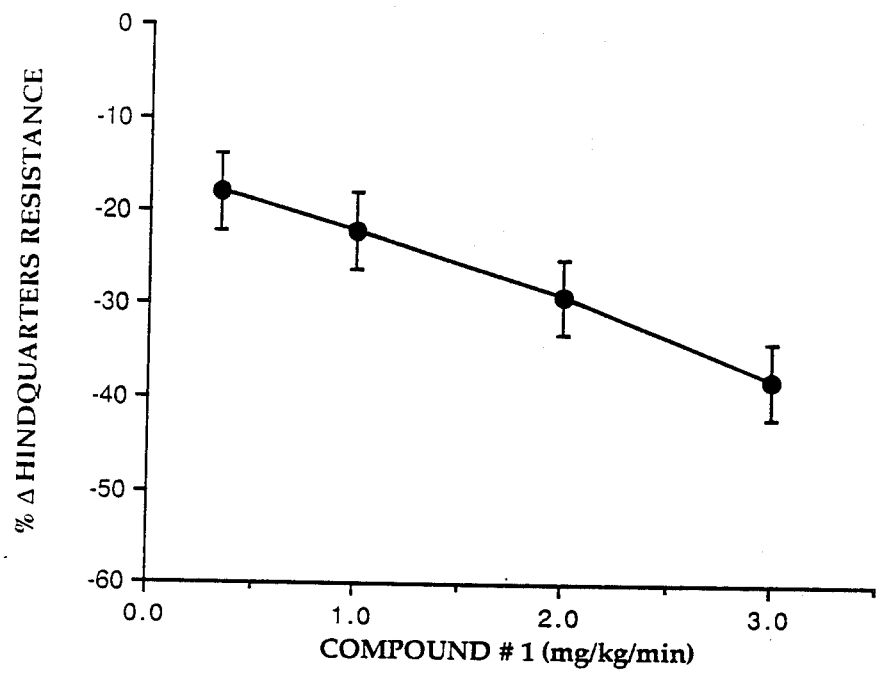
FIG. 13 is a graph showing effects of Compound #1 on hindquarters vascular resistance in anesthetized normotensive rats.
Figure 14:
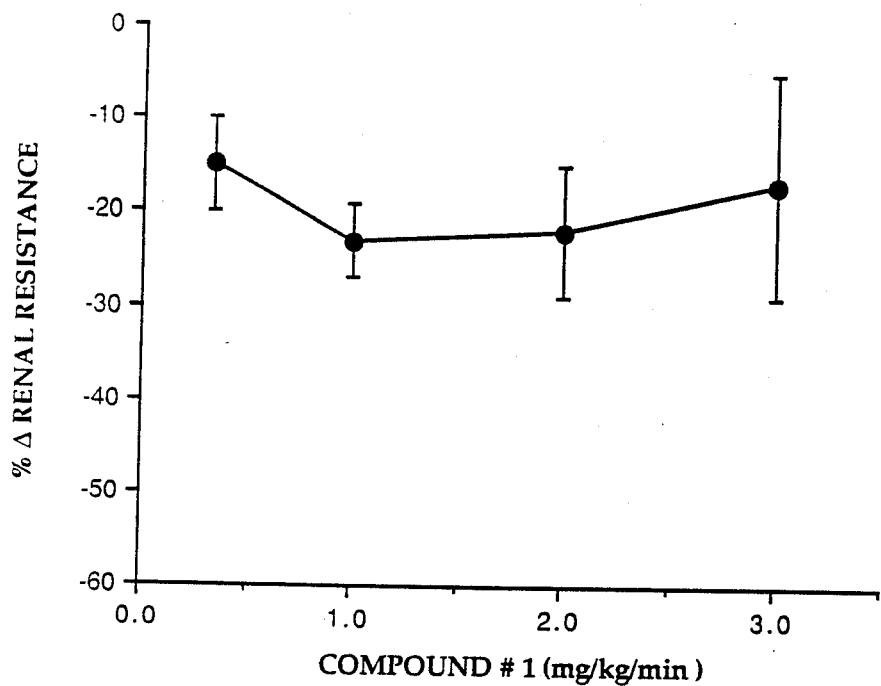
FIG. 14 is a graph showing effects of Compound #1 on renal vascular resistance in anesthetized normotensive rats.

The effects of Compound #1 administration on mean arterial pressure (MAP) and heart rate (HR) are illustrated in Tables XX, XXI and FIG. 7. A dose-dependent fall in MAP was observed, which was associated with a slight tachycardia. The absolute changes in MAP are shown in Table XXII and FIG. 8. Mesenteric blood flow increased at all doses of Compound #1 and hindquarters flow increased at 0.34 and 1.0 mg/kg/min, but this effect was not evident at higher doses (Tables XXIII, XXIV and FIGS. 9,10). Renal blood flow was unchanged at lower doses but increased at doses of Compound #1 which dropped blood pressure substantially (Table XXV, FIG. 11). These changes in regional blood flow were then used to calculate changes in regional vascular resistance. Dose-dependent reductions in resistance were observed in both the mesenteric and hindquarters beds (Tables XXVI, XXVII and FIGS. 12,13). A decrease in renal resistance was observed at the lower doses of Compound #1, but further reductions were not seen at the higher doses (Table XXVIII, FIG. 14). These data indicate that decreases in regional vascular resistance contribute to the fall in pressure produced by Compound #1, with a greater vasodilation in the mesenteric and skeletal muscle beds compared to the renal bed.

EXAMPLE IV

Compound #1 was administered intragastrically to spontaneously hypertensive rats (SHR) to determine blood pressure lowering activity in a hypertensive model. Spontaneously hypertensive rats (12-14 weeks old) were obtained from Charles River Laboratories. The animals were anesthetized with 35 mg/kg of Brevital Sodium (Lilly) given I.P. Catheters (PE 50) were sterilized, filled with heparinized saline (30 U/ml) and then implanted in the right femoral artery. The arterial line was sewn to the leg muscles, threaded under the skin and then exteriorized behind the scapulae. A wire plug was inserted into the end of the catheter until blood pressure and heart rate recordings were made.

Pulse pressure and heart rate were recorded on a Gould system as described in Example I. Mean arterial pressure was calculated according to the following formula: MAP=Diastolic Pressure+⅓ Pulse Pressure. The animals were conscious during blood pressure recordings and were unrestrained.

Compound #1 was prepared for administration as described in Example I. The compound was administered intragastrically to the rats using a Perfektum animal feeding needle (16G-2" straight) after the animals were lightly anesthetized with ether.

Figure 16:
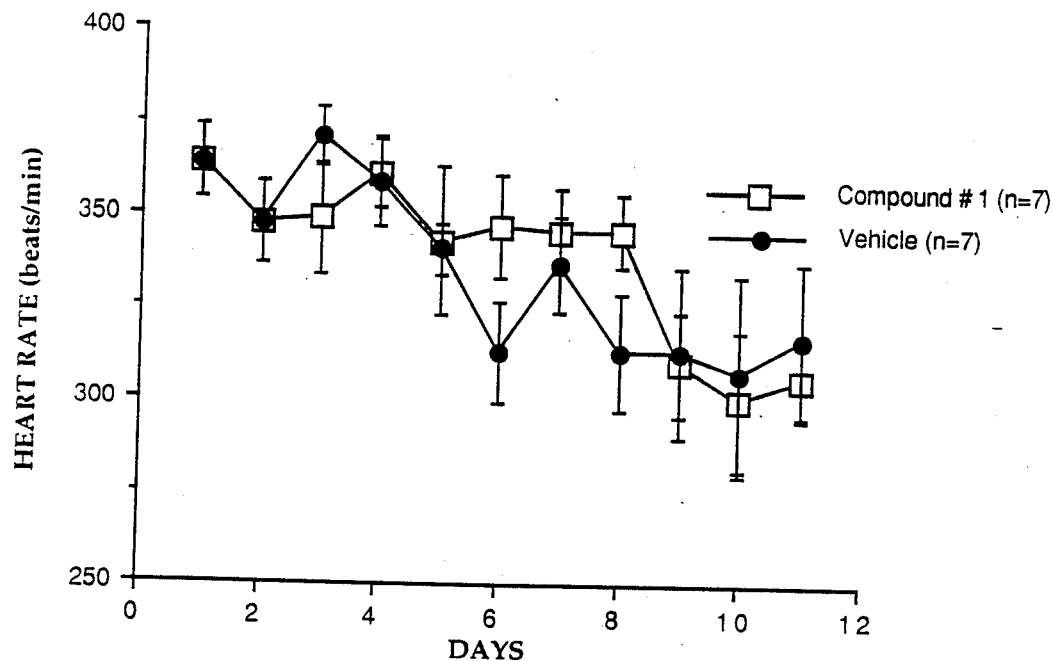
FIG. 16 is a graph showing the effect on heart rate when Compound #1 is administered intragastrically to conscious spontaneously hypertensive rats.
Figure 17:
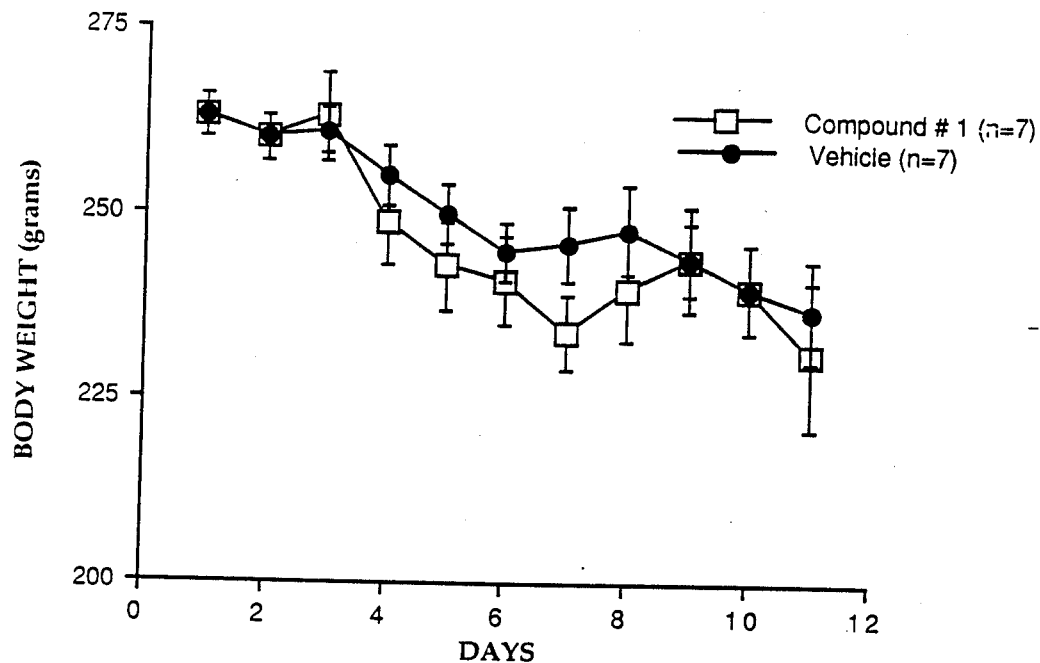
FIG. 17 is a graph showing effect on body weight when Compound #1 is administered intragastrically to conscious spontaneously hypertensive rats.

One day following implantation of the catheters, baseline measurements of MAP and HR were measured between 12 and 2 pm for two consecutive days. For these measurements, the rats were removed from their cages and placed in large, cardboard boxes 45 minutes prior to beginning the recordings to allow the animals to acclimate to the new environment. MAP and HR were then recorded for one hour. The values for these parameters were calculated every 10 minutes and then averaged over the one hour sampling period. One-half of the animals were then randomly selected to receive 200 mg/kg/day of Compound #1 intragastrically for five days, followed by a four day recovery period during which the rats were administered an equal volume of distilled water. The other half of the rats received distilled water throughout the study. The animals were dosed each morning and mean arterial pressure and heart rate were measured 4-5 hours later. Results are reported in Tables XXIX-XXXVII and in FIGS. 15-17.

| XXIX. MEAN ARTERIAL PRESSURE IN SPONTANEOUSLY HYPERTENSIVE RATS PRIOR TO VEHICLE/DRUG TREATMENT | | |
|---|---|---|
| | MAP (mmHg) | |
| RAT | DAY 1 | DAY 2 |
| 1 | 130 | 150 |
| 2 | 159 | 139 |
| 3 | 124 | 151 |
| 4 | 149 | 140 |
| 5 | 179 | 139 |
| 6 | 161 | 129 |
| 7 | 143 | 132 |
| 8 | 133 | 125 |
| 9 | 138 | 126 |
| 10 | 141 | 141 |
| 11 | 134 | 123 |
| 12 | 128 | 148 |
| 13 | 165 | 159 |
| 14 | 160 | 147 |
| | 146 ± 4 | 139 ± 3 |

| XXX. EFFECTS OF VEHICLE ADMINISTRATION ON MEAN ARTERIAL PRESSURE IN SPONTANEOUSLY HYPERTENSIVE RATS | | | | | | | | | |
|---|---|---|---|---|---|---|---|---|---|
| | MAP (mmHg) | | | | | | | | |
| DAY | RAT1 | RAT2 | RAT3 | RAT4 | RAT12 | RAT13 | RAT14 | MEAN | SEM |
| 3 | 145 | 133 | 162 | 153 | 158 | 176 | 164 | 156 | 5 |
| 4 | 154 | 157 | 151 | 147 | 162 | 160 | — | 155 | 2 |
| 5 | 145 | 153 | 151 | 143 | 150 | 167 | — | 152 | 4 |
| 6 | 135 | 139 | 161 | 130 | 154 | 156 | — | 146 | 5 |
| 7 | 143 | 153 | 137 | 169 | 131 | — | — | 147 | 7 |
| 8 | 140 | — | 154 | 151 | 141 | — | — | 147 | 4 |
| 9 | 153 | 126 | 151 | 125 | 154 | — | — | 142 | 7 |
| 10 | 168 | 138 | 153 | 148 | 121 | — | — | 146 | 8 |
| 11 | 147 | 161 | 179 | — | 136 | — | — | 156 | 9 |

XXXI. EFFECTS OF ORAL ADMINISTRATION OF COMPOUND #1 (200 MG/KG/DAY) ON MEAN ARTERIAL PRESSURE IN SPONTANEOUSLY HYPERTENSIVE RATS

| DAY* | RAT5 | RAT6 | RAT7 | RAT8 | RAT9 | RAT10 | RAT11 | MEAN | SEM |
|---|---|---|---|---|---|---|---|---|---|
| 3 | 159 | 151 | 147 | 144 | 143 | 139 | 137 | 146 | 3 |
| 4 | 108 | 151 | 119 | 149 | 139 | 117 | 140 | 132 | 6 |
| 5 | 122 | 128 | 131 | 121 | 96 | 100 | 126 | 118 | 5 |
| 6 | 141 | 124 | 107 | 126 | 114 | 106 | 137 | 122 | 5 |
| 7 | 124 | 121 | 119 | 125 | 120 | — | 137 | 124 | 3 |
| 8 | 152 | 130 | 142 | 152 | 121 | — | 151 | 141 | 5 |
| 9 | 141 | 121 | 137 | 142 | 133 | — | 140 | 136 | 3 |
| 10 | 120 | 141 | 120 | 132 | — | — | 135 | 130 | 4 |
| 11 | 139 | 115 | 167 | 150 | — | — | 133 | 141 | 9 |

*Day 3-7 - 200 mg/kg/day
*Day 8-11 - Recovery

XXXII. HEART RATE IN SPONTEANOUSLY HYPERTENSIVE RATS PRIOR TO VEHICLE/DRUG TREATMENT

| RAT | HEART RATE (beats/min) DAY 1 | DAY 2 |
|---|---|---|
| 1 | 333 | 396 |
| 2 | — | 349 |
| 3 | 300 | 351 |
| 4 | 400 | 371 |
| 5 | 387 | 376 |
| 6 | — | 351 |
| 7 | 376 | 329 |
| 8 | 339 | 310 |
| 9 | 346 | 307 |
| 10 | 402 | 380 |
| 11 | 366 | 300 |
| 12 | 380 | 359 |
| 13 | — | 354 |
| 14 | 379 | 346 |
|  | 364 ± 10 | 348 ± 11 |

XXXV. BODY WEIGHT IN SPONTANEOUSLY HYPERTENSIVE RATS PRIOR TO VEHICLE/DRUG TREATMENT

| RAT | BODY WEIGHT (grams) DAY 1 | DAY 2 |
|---|---|---|
| 1 | 256 | 251 |
| 2 | 266 | 256 |
| 3 | 264 | 266 |
| 4 | 268 | 268 |
| 5 | 241 | 230 |
| 6 | 266 | 264 |
| 7 | 271 | 268 |
| 8 | 263 | 263 |
| 9 | 258 | 259 |
| 10 | 287 | 278 |
| 11 | 258 | 261 |
| 12 | 265 | 261 |
| 13 | 264 | 257 |
| 14 | 261 | 260 |
|  | 263 ± 3 | 260 ± 3 |

XXXIII. EFFECTS OF VEHICLE ADMINISTRATION ON HEART RATE IN SPONTANEOUSLY HYPERTENSIVE RATS

| DAY | RAT1 | RAT2 | RAT3 | RAT4 | RAT12 | RAT13 | RAT14 | MEAN | SEM |
|---|---|---|---|---|---|---|---|---|---|
| 3 | 400 | 364 | 400 | 359 | 367 | 341 | 364 | 371 | 8 |
| 4 | 374 | 380 | 333 | 394 | 354 | 316 | — | 359 | 12 |
| 5 | 341 | 336 | 324 | 367 | 350 | 326 | — | 341 | 7 |
| 6 | 263 | 277 | 298 | 330 | 350 | 342 | — | 313 | 14 |
| 7 | 289 | 321 | 333 | 383 | 347 | 348 | — | 337 | 13 |
| 8 | 309 | 263 | 292 | 349 | 371 | 294 | — | 313 | 16 |
| 9 | 298 | 283 | — | 358 | — | — | — | 313 | 23 |
| 10 | 340 | 259 | — | 366 | 262 | — | — | 307 | 27 |
| 11 | 279 | 342 | — | — | 332 | — | — | 317 | 21 |

XXXIV. EFFECTS OF ORAL ADMINISTRATION OF COMPOUND #1 (200 MG/KG/DAY) ON HEART RATE ON SPONTANEOUSLY HYPERTENSIVE RATS

| DAY* | RAT5 | RAT6 | RAT7 | RAT8 | RAT9 | RAT10 | RAT11 | MEAN | SEM |
|---|---|---|---|---|---|---|---|---|---|
| 3 | 351 | 391 | 400 | 325 | 344 | 282 | 351 | 349 | 15 |
| 4 | 383 | 391 | 362 | 355 | 328 | — | 349 | 361 | 9 |
| 5 | 370 | 386 | 398 | 326 | 273 | — | 305 | 343 | 20 |
| 6 | 343 | 396 | 343 | 299 | 370 | — | 331 | 347 | 14 |
| 7 | 322 | 365 | — | 319 | 350 | — | 375 | 346 | 11 |
| 8 | 337 | 350 | 381 | 364 | 321 | — | 324 | 346 | 10 |
| 9 | 325 | 329 | — | 343 | 274 | — | 277 | 310 | 14 |
| 10 | 266 | 366 | 289 | 315 | — | — | 265 | 300 | 19 |
| 11 | 279 | 296 | — | 330 | — | — | 318 | 306 | 11 |

*Day 3-7 - 200 mg/kg/day
*Day 8-11 - Recovery

XXXVI. EFFECTS OF VEHICLE ADMINISTRATION ON BODY WEIGHT IN SPONTANEOUSLY HYPERTENSIVE RATS

| DAY | BODY WEIGHT (grams) | | | | | | | MEAN | SEM |
|---|---|---|---|---|---|---|---|---|---|
| | RAT1 | RAT2 | RAT3 | RAT4 | RAT12 | RAT13 | RAT14 | | |
| 3 | 253 | 271 | 265 | 267 | 259 | 257 | 255 | 261 | 3 |
| 4 | 235 | 266 | 254 | 265 | 259 | 257 | 248 | 255 | 4 |
| 5 | 231 | 264 | 248 | 259 | 252 | 255 | 243 | 250 | 4 |
| 6 | 224 | 251 | 250 | 259 | 245 | 246 | 246 | 245 | 4 |
| 7 | 223 | 252 | 241 | 261 | 246 | 254 | — | 246 | 5 |
| 8 | 225 | 255 | 243 | 267 | 243 | 252 | — | 248 | 6 |
| 9 | 224 | 254 | 239 | 261 | 244 | 240 | — | 244 | 5 |
| 10 | 230 | 261 | 234 | 255 | 231 | 229 | — | 240 | 6 |
| 11 | 234 | 269 | 235 | 241 | 221 | 219 | — | 237 | 7 |

XXXVII. EFFECTS OF ORAL ADMINISTRATION OF COMPOUND #1 (200 MG/KG/DAY) ON BODY WEIGHT IN SPONTANEOUSLY HYPERTENSIVE RATS

| Day* | BODY WEIGHT (grams) | | | | | | | Mean | SEM |
|---|---|---|---|---|---|---|---|---|---|
| | Rat5 | Rat6 | Rat7 | Rat8 | Rat9 | Rat10 | Rat11 | | |
| 3 | 233 | 270 | 273 | 262 | 259 | 283 | 263 | 263 | 6 |
| 4 | 215 | 265 | 261 | 250 | 253 | 256 | 242 | 249 | 6 |
| 5 | 214 | 259 | 258 | 241 | 243 | 246 | 241 | 243 | 6 |
| 6 | 217 | 262 | 255 | 252 | 229 | 232 | 237 | 241 | 6 |
| 7 | 224 | 253 | 242 | 245 | 217 | 229 | 228 | 234 | 5 |
| 8 | 225 | 261 | 252 | 254 | 219 | — | 226 | 240 | 7 |
| 9 | 231 | 262 | 253 | 262 | 225 | — | 231 | 244 | 7 |
| 10 | 226 | 260 | 249 | 246 | 231 | — | 278 | 240 | 6 |
| 11 | 207 | 254 | 256 | 229 | — | — | 210 | 231 | 10 |

Day* 3-7 - 200 mg/kg/day
Day* 8-11 - Recovery

Figure 15:
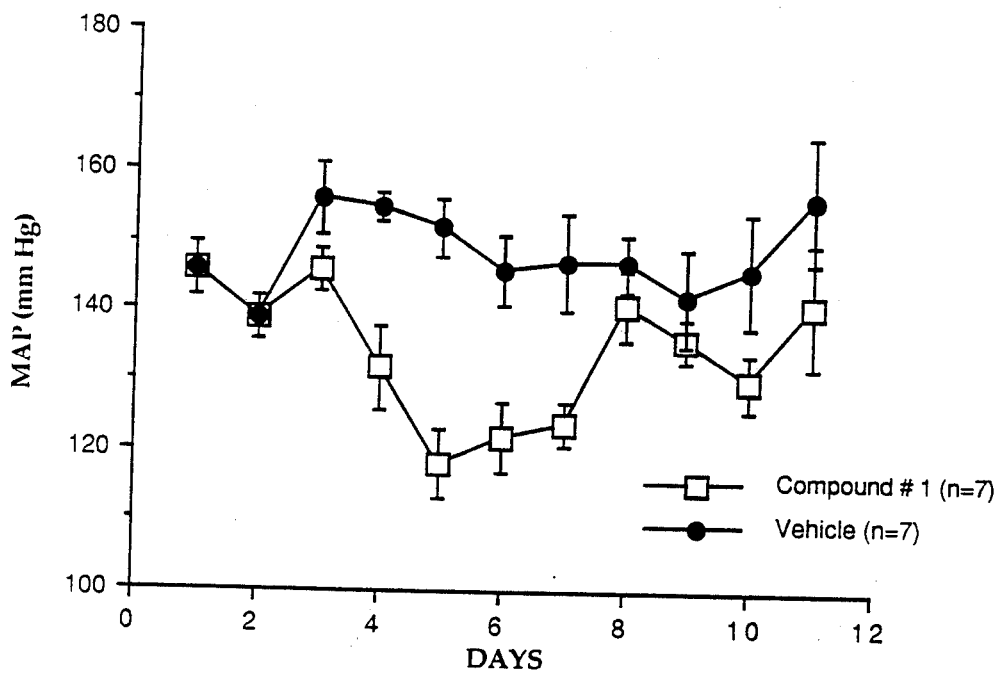
FIG. 15 is a graph showing effect on mean arterial pressure when Compound #1 is administered intragastrically to conscious spontaneously hypertensive rats.

Mean arterial pressure in this group of spontaneously hypertensive rats (SHRs) averaged 146 and 139 mmHg, respectively, on the two days pressures were measured prior to beginning the vehicle or drug treatments (Table XXIX). Variations in MAP of this degree are quite common in studies where blood pressure is measured in a conscious, unrestrained spontaneously hypertensive rat. Intragastric administration of the vehicle (distilled water) for nine days did not lower MAP (Table XXX, FIG. 15). In the rats treated with Compound #1 at 200 mg/kg/day, MAP was significantly reduced to a low of 118 mmHg on the third day of drug treatment (Table XXXI, FIG. 15). A mean pressure of 118 mmHg is similar to the mean pressure recorded in Wistar Kyoto rats, the strain of animal which is typically used as the control for the SHR. This reduction in MAP was rapidly and completely reversed, since on the first day of vehicle treatment in these animals, MAP was not significantly different from MAP in the vehicle-treated group (FIG. 15). Heart rate in the vehicle-treated rats was reduced from an average of 348 beats per/min on Day 2 to 317 beats/min on Day 11 (Tables XXXII and XXXIII, FIG. 16). Heart rate in Compound #1 treated rats was reduced to 306 beats/min, a reduction which was similar to the fall in heart rate observed in the vehicle-treated group (Table XXXIV, FIG. 16). Thus, the blood pressure-lowering effects of Compound #1 administered chronically are not associated with tachycardia. Reflex tachycardia can sometimes be a problem with the administration of peripheral vasodilators, particularly when pressure drops rapidly.

Body weight in the vehicle and drug-treated rats was monitored throughout the study to detect any potential adverse effects of the drug on the general health of the animals. Body weight in this group of SHRs averaged 263 and 260 grams, respectively, on the two days prior to beginning the vehicle/drug treatment (Table XXXV). At the end of the study, body weight in the vehicle treated rats had fallen to 237 grams, whereas body weight in the Compound #1 treated group averaged 231 grams when the study was terminated (Tables XXXVI and XXXVII, FIG. 17). Therefore administration of the drug did not appear to adversely effect the general health of the treated rats.

In summary, oral administration of Compound #1 effectively reduced mean arterial blood pressure in SHRs to normotensive levels. This reduction was rapidly and completely reversed when the drug treatment was terminated and the animals were allowed to recover. Most importantly, this fall in pressure in the SHR was not accompanied by reflex tachycardia. Oral administration of Compound #1 also did not appear to have an adverse effect on the general health of the treated rats. These data indicate that the drug is both effective and well tolerated at a dose of 200 mg/kg/day.

Examples I-IV demonstrate that Compound #1 is effective on acute treatment therapies in simultaneously lowering blood pressure and promoting sodium excretion when infused intravenously into anesthetized rats. The mechanism of this depressor and natriuretic action may be mediated by cGMP since an increase in plasma cGMP levels and the urinary excretion of cGMP occur in parallel with these actions. Although an increase in cAMP plasma levels and the urinary excretion of cAMP also occurred in the Compound #1 infused rats, these changes did not correlate well with the depressor and natriuretic actions of this compound. When Compound #1 is administered chronically to spontaneously hypertensive rats, mean arterial blood pressure is reduced to normotensive levels without any sign of reflex tachycardia. The fall in mean arterial pressure observed when Compound #1 is infused into anesthetized rats appears to be due to reductions in regional vascular resistance, with more vasodilation in the mesenteric and hindquarters bed compared to the renal bed. These data indicate that Compound #1 may be an effective antihypertensive agent in man.

What is claimed is:

1. A method for treatment of hypertension in a host in need of said treatment by administering a therapeutically-effective amount of an antihypertensive compound selected from the group consisting of a family of compounds of formula

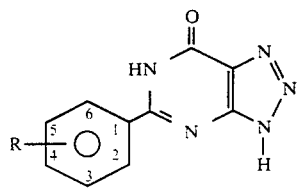

wherein R represents one or more groups selected from the group consisting of alkyl, alkenyl, alkoxy, alkenyloxy, aralkyl and aralkoxy, the alkyl portion of any of said groups being in linear or branched configuration and containing one to about twenty carbon atoms; and or a pharmaceutically-acceptable salt thereof; with the proviso that at least one of R is an alkoxy group.

2. The method of claim 1 wherein R represents one or more groups selected from the group consisting of alkyl, alkenyl, alkoxy, alkenyloxy, phenylalkyl and phenylalkoxy, the alkyl portion of any of said groups being in linear or branched configuration and containing one to about twenty carbon atoms; or a pharmaceutically-acceptable salt thereof; with the proviso that at least one of R is a linear or branched alkoxy group having one to about twenty carbon atoms.

3. The method of claim 2 wherein the alkyl portion of any of said R groups is linear or branched and contains one to about ten carbon atoms.

4. The method of claim 3 wherein R represents one or more groups selected from the group consisting of methyl, ethyl, n-propyl, isopropyl, n-butyl, iso-butyl, sec-butyl, tert-butyl, n-pentyl, iso-pentyl, neopentyl, n-hexyl, n-heptyl, ethenyl, n-propenyl, iso-propenyl, methoxy, ethoxy, n-propoxy, isopropoxy, n-butoxy, iso-butoxy, sec-butoxy, tert-butoxy, n-pentyloxy, iso-pentyloxy, neopentyloxy, n-hexyloxy, n-heptyloxy, allyloxy, phenmethyl, phenethyl, phenpropyl, benzyloxy, phenethoxy and phenpropoxy; or a pharmaceutically-acceptable salt thereof; with the proviso that at least one of R is an alkoxy group selected from the group consisting of methoxy, ethoxy, n-propoxy, iso-propoxy, n-butoxy, iso-butoxy, sec-butoxy, tert-butoxy, n-pentyloxy, iso-pentyloxy, neopentyloxy, n-hexyloxy, n-heptyloxy, allyloxy and benzyloxy.

5. The method of claim 4 wherein R represents one or more groups selected from the group consisting of methyl, ethyl, n-propyl, isopropyl, n-butyl, methoxy, ethoxy, n-propoxy, iso-propoxy, n-butoxy, iso-butoxy, sec-butoxy, tert-butoxy, n-pentyloxy, iso-pentyloxy, neopentyloxy, n-hexyloxy, allyloxy and benzyloxy; or a pharmaceutically-acceptable salt thereof; with the proviso that R includes at least one or two alkoxy groups attached at the 2-, 4- or 5- positions of the phenyl ring.

6. The method of claim 5 wherein said antihypertensive compound is selected from the group of compounds consisting of
8-aza-2-(2-n-propoxyphenyl)purin-6-one;
8-aza-2-(2-methoxyphenyl)purin-6-one;
8-aza-2-(2-ethoxyphenyl)purin-6-one;
8-aza-2-(2-isopropoxyphenyl)purin-6-one;
8-aza-2-(2-n-butoxyphenyl)purin-6-one;
8-aza-2-(2-isobutoxyphenyl)purin-6-one;
8-aza-2-(2-sec-butoxyphenyl)purin-6-one;
8-aza-2-(2-tert-butoxyphenyl)purin-6-one;
8-aza-2-(2-n-pentyloxyphenyl)purin-6-one;
8-aza-2-(2-isopentyloxyphenyl)purin-6-one;
8-aza-2-(2-n-hexyloxyphenyl)purin-6-one;
8-aza-2-(2-benzyloxyphenyl)purin-6-one;
8-aza-2-(2,4-dimethoxyphenyl)purin-6-one;
8-aza-2-(2,5-dimethoxyphenyl)purin-6-one;
8-aza-2-(2,5-dibenzyloxyphenyl)purin-6-one;
8-aza-2-(5-benzyloxy-2-methoxyphenyl)purin-6-one;
8-aza-2-(5-tert-butyl-2-methoxyphenyl)purin-6-one;
8-aza-2-(2-methoxy-5-methylphenyl)purin-6-one;
8-aza-2-(2-methoxy-3,5-dimethylphenyl)purin-6-one; and
8-aza-2-(2-allyloxyphenyl)purin-6-one.

7. The method of claim 5 wherein R is a single alkoxy group selected from the group consisting of methoxy, ethoxy, n-propoxy, n-butoxy and n-pentyloxy, and attached at the 2-position phenyl ring relative to attachment of the phenyl ring to the 8-azapurine-6-one nucleus.

8. The method of claim 7 wherein said antihypertensive compound is selected from the group consisting of
8-aza-2-(2-n-propoxyphenyl)purin-6-one;
8-aza-2-(2-methoxyphenyl)purin-6-one;
8-aza-2-(2-ethoxyphenyl)purin-6-one;
8-aza-2-(2-n-butoxyphenyl)purin-6-one; and
8-aza-2-(2-n-pentyloxyphenyl)purin-6-one.

9. The method of claim 8 wherein said antihypertensive compound is 8-aza-2-(2-n-propoxyphenyl)-purin-6-one.

10. A method for treating a host afflicted with congestive heart failure or edema resulting from hypertension, said method comprising administering a therapeutically-effective amount of an active compound having both antihypertensive and fluid-volume-reducing properties, said compound selected from the group consisting of a family of compounds of the formula

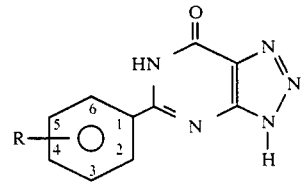

wherein R represents one or more groups selected from the group consisting of alkyl, alkenyl, alkoxy, alkenyloxy, aralkyl and aralkoxy, the alkyl portion of any of said groups being in linear or branched configuration and containing one to about twenty carbon atoms; and a pharmaceutically-acceptable salt thereof; with the proviso that at least one of R is an alkoxy group.

11. The method of claim 10 wherein R represents one or more groups selected from the group consisting of alkyl, alkenyl, alkoxy, alkenyloxy, phenylalkyl and phenylalkoxy, the alkyl portion of any of said groups being in linear or branched configuration and containing one to about twenty carbon atoms; or a pharmaceutically-acceptable salt thereof; with the proviso that at least one of R is a linear or branched alkoxy group having one to about twenty carbon atoms.

12. The method of claim 11 wherein the alkyl portion of any of said R groups is linear or branched and contains one to about ten carbon atoms.

13. The method of claim 12 wherein R represents one or more groups selected from the group consisting of methyl, ethyl, n-propyl, isopropyl, n-butyl, iso-butyl, sec-butyl, tert-butyl, n-pentyl, iso-pentyl, neopentyl, n-hexyl, n-heptyl, ethenyl, n-propenyl, iso-propenyl, methoxy, ethoxy, n-propoxy, isopropoxy, n-butoxy, iso-butoxy, sec-butoxy, tert-butoxy, n-pentyloxy, iso-pentyloxy, neopentyloxy, n-hexyloxy, n-heptyloxy, allyloxy, phenmethyl, phenethyl, phenpropyl, benzyloxy, phenethoxy and phenpropoxy; or a pharmaceutically-acceptable salt thereof; with the proviso that at least one of R is an alkoxy group selected from the group consisting of methoxy, ethoxy, n-propoxy, iso-propoxy, n-butoxy, iso-butoxy, sec-butoxy, tert-butoxy, n-pentyloxy, iso-pentyloxy, neopentyloxy, n-hexyloxy, n-heptyloxy, allyloxy and benzyloxy.

14. The method of claim 13 wherein R represents one or more groups selected from the group consisting of methyl, ethyl, n-propyl, isopropyl, n-butyl, methoxy, ethoxy, n-propoxy, iso-propoxy, n-butoxy, iso-butoxy, sec-butoxy, tert-butoxy, n-pentyloxy, iso-pentyloxy, neopentyloxy, n-hexyloxy, allyloxy and benzyloxy; or a pharmaceutically-acceptable salt thereof; with the proviso that R includes at least one or two alkoxy groups attached at the 2-, 4- or 5- positions of the phenyl ring.

15. The method of claim 14 wherein said antihypertensive compound is selected from the group of compounds consisting of 8-aza-2-(2-n-propoxyphenyl)purin-6-one;
8-aza-2-(2-methoxyphenyl)purin-6-one;
8-aza-2-(2-ethoxyphenyl)purin-6-one;
8-aza-2-(2-isopropoxyphenyl)purin-6-one;
8-aza-2-(2-n-butoxyphenyl)purin-6-one;
8-aza-2-(2-isobutoxyphenyl)purin-6-one;
8-aza-2-(2-sec-butoxyphenyl)purin-6-one;
8-aza-2-(2-tert-butoxyphenyl)purin-6-one;
8-aza-2-(2-n-pentyloxyphenyl)purin-6-one;
8-aza-2-(2-isopentyloxyphenyl)purin-6-one;
8-aza-2-(2-n-hexyloxyphenyl)purin-6-one;
8-aza-2-(2-benzyloxyphenyl)purin-6-one;
8-aza-2-(2,4-dimethoxyphenyl)purin-6-one;
8-aza-2-(2,5-dimethoxyphenyl)purin-6-one;
8-aza-2-(2,5-dibenzyloxyphenyl)purin-6-one;
8-aza-2-(5-benzyloxy-2-methoxyphenyl)purin-6-one;
8-aza-2-(5-tert-butyl-2-methoxyphenyl)purin-6-one;
8-aza-2-(2-methoxy-5-methylphenyl)purin-6-one;
8-aza-2-(2-methoxy-3,5-dimethylphenyl)purin-6-one; and
8-aza-2-(2-allyloxyphenyl)purin-6-one.

16. The method of claim 14 wherein R is a single alkoxy group selected from the group consisting of methoxy, ethoxy, n-propoxy, n-butoxy and n-pentyloxy, and attached at the 2-position phenyl ring relative to attachment of the phenyl ring to the 8-azapurine-6-one nucleus.

17. The method of claim 16 wherein said antihypertensive compound is selected from the group consisting of 8-aza-2-(2-n-propoxyphenyl)purin-6-one;
8-aza-2-(2-methoxyphenyl)purin-6-one;
8-aza-2-(2-ethoxyphenyl)purin-6-one;
8-aza-2-(2-n-butoxyphenyl)purin-6-one; and
8-aza-2-(2-n-pentyloxyphenyl)purin-6-one.

18. The method of claim 17 wherein said antihypertensive compound is 8-aza-2-(2-n-propoxyphenyl)purin-6-one.

* * * * *